United States Patent
Di Cera et al.

(10) Patent No.: US 8,940,297 B2
(45) Date of Patent: Jan. 27, 2015

(54) EXPRESSION OF THROMBIN VARIANTS

(75) Inventors: Enrico Di Cera, Ladue, MO (US);
  Andras Gruber, Portland, OR (US);
  Prafull Gandhi, St. Louis, MO (US);
  Leslie Pelc, Freeburg, IL (US); Nicola Pozzi, St. Louis, MO (US); David Collier Wood, Wildwood, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 13/331,109

(22) Filed: Dec. 20, 2011

(65) Prior Publication Data

US 2012/0164129 A1  Jun. 28, 2012

Related U.S. Application Data

(60) Provisional application No. 61/426,385, filed on Dec. 22, 2010.

(51) Int. Cl.
  *C12N 9/74* (2006.01)
  *A61K 38/48* (2006.01)

(52) U.S. Cl.
  CPC ............ *C12N 9/6429* (2013.01); *A61K 38/4833* (2013.01); *C12Y 304/21005* (2013.01)
  USPC ........................................ 424/94.64; 435/214

(58) Field of Classification Search
  None
  See application file for complete search history.

(56) References Cited

U.S. PATENT DOCUMENTS

| | | | |
|---|---|---|---|
| 5,297,441 A | 3/1994 | Smith et al. | |
| 5,387,744 A | 2/1995 | Curtiss et al. | |
| 5,888,799 A | 3/1999 | Curtiss | |
| 6,024,961 A | 2/2000 | Curtiss et al. | |
| 6,413,737 B1 * | 7/2002 | Olsen et al. | 435/226 |
| 6,706,512 B2 * | 3/2004 | Gruber et al. | 435/226 |
| 7,223,583 B2 * | 5/2007 | Gruber et al. | 435/226 |
| 2006/0205041 A1 | 9/2006 | Frye et al. | |
| 2007/0148722 A1 | 6/2007 | Nowak et al. | |
| 2010/0158890 A1 | 6/2010 | Tanaka et al. | |

FOREIGN PATENT DOCUMENTS

| | | | |
|---|---|---|---|
| WO | 9855130 | 12/1998 | |
| WO | 9950454 | 10/1999 | |
| WO | 02100337 | 12/2002 | |
| WO | 03014381 | 2/2003 | |
| WO | WO/2008/045148 | * 4/2008 | C12N 9/64 |

OTHER PUBLICATIONS

NCBI Reference Sequence: NP_000497.1.*
U.S. Appl. No. 07/860,701, filed Mar. 1992, Wasseem, M.*
Ian Hunt, From gene to protein: a review of new and enabling technologies for multi-parallel protein expression, Protein Expression and Purification, 40 (2005) 1-22.*
Chen et al., Partially Purified *Echis carinatus* Venom Cleaves Active-Site-Mutated Bovine Prothrombin at Two Sites, Thrombosis Research, 85(5):369-375 (1997).*
Di Cera, Thrombin, Mol. Aspects of Med., 29(2008)203-254.*
Feistritzer, et al., Protective Signaling by Activated Protein C Is Mechanistically Linked to Protein C Activation on Endothelial Cells(2006) J. Biol. Chem. 281:20077-20084.
Gruber, et al. The Thrombin Mutant W215A/E217A Shows Safe and Potent Anticoagulant and Antithrombotic Effects in Vivo(2002) J. Biol. Chem. 277:27581-27584.
Gruber, et al., Limited generation of activated protein C during infusion of the protein C activator thrombin analog W215A/E217A in primates, (2006) Journal of Thrombosis and Haemostasis, 4: 392-397.
Gruber, et al., Relative antithrombotic and antihemostatic effects of protein C activator versus low-molecular-weight heparin in primates; (2007) Blood 109:3733-3740.
Cantwell, et al., Rational Design of a Potent Anticoagulant Thrombin; Journal of Biological Chemistry, vol. 275. No. 51, Dec. 2000, pp. 39827-39830.
Arosio, et al., Mutation of W215 Compromises Thrombin Cleavage of Fibrinogen, but Not of PAR-1 or Protein C; (2000) Biochemistry 39:8095-8101.
Londono, et al., Immunisation of mice using Salmonella typhimurium expressing human papillomavirus type 16 E7 epitopes inserted into hepatitis B virus core antigen; (1996) Vaccine, vol. 14, No. 6:545-552.
Marino, et al., Engineering Thrombin for Selective Specificity toward Protein C and PAR1, The Journal of Biological Chemistry vol. 285, No. 25, pp. 19145-19152, Jun. 18, 2010.
Nardelli-Haefliger, et al., Oral and Rectal Immunization of Adult Female Volunteers with a Recombinant Attenuated *Salmonella typhi* Vaccine Strain, Infection and Immunity, Dec. 1996, p. 5219-5224.
Schödel, et al., Immunization with Hybrid Hepatitis B Virus Core Particles Carrying Circumsporozoite Antigen Epitopes Protects Mice Against *Plasmodium yoelii* Challenge; (1997) Behring Inst. Mitt., 98:114-119.

(Continued)

*Primary Examiner* — Maury Audet
*Assistant Examiner* — Joseph Fischer
(74) *Attorney, Agent, or Firm* — Armstrong Teasdale LLP

(57) ABSTRACT

One aspect of the invention contemplates a mutant E-WE thrombin precursor that contains the SEQ ID NO:1 amino acid residue sequence. Another aspect contemplates a thrombin precursor that contains the amino acid residue sequence Asp/Glu-Gly-Arg at positions 325, 326 and 327 based on the preprothrombin sequence. A third aspect contemplates a thrombin precursor that contains the SEQ ID NO:1 amino acid residue sequence as well as the amino acid residue sequence Asp/Glu Gly Arg at positions 325, 326 and 327 based on the preprothrombin sequence. Also contemplated is a composition that contains an effective amount of mutant thrombin dissolved or dispersed in a pharmaceutically acceptable carrier. A method is also disclosed for enhancing treating and preventing thrombosis in a mammal in need using that composition.

9 Claims, No Drawings

(56) References Cited

OTHER PUBLICATIONS

Tacket, et al., Safety and Immunogenicity in Humans of an Attenuated *Salmonella typhi* Vaccine Vector Strain Expressing Plasmid-Encoded Hepatitis B Antigens Stabilized by the Asd-Balanced Lethal Vector System(1997) Infection and Immunity, 65(8):3381-3385.
Ulrich, et al., Core Particles of Hepatitis B Virus As Carrier for Foreign Epitopes, (1998) Advances in Virus Research, vol. 50:141-182.
Berny, et al.,Thrombin Mutant W215A/E217A Acts as a Platelet GPlb Antagonist (2008) Arterioscler, Thromb. Vasc. Biol. 18:329-334.
Degen, et al., Characterization of the Complementary Deoxyribonucleic Acid and Gene Coding for Human Prothrombin; (1983) Biochemistry 22:2087-2097.
Wu, et al., Single Amino Acid Substitutions Dissociate Fibrinogen-clotting and Thrombomodulin-binding activities of Human Thrombin, Proc. Natl. Acad. Sci. USA, vol. 88, pp. 6775-6779, Aug. 1991.
Hanson, et al., Antithrombotic Effects of Thrombin-induced Activation of Endogenous Protein C in Primages; J. Clin. Invest, vol. 92, pp. 2003-2012, Oct. 1993.
Kogan, et al., Protein C activator from the venom of *Agkistrodon blomhoffi* ussuriensis retards thrombus formation in the arteriovenous shunt in rats., Thromb Res. Jun. 1, 1993;70(5):385-93.
Gibbs, Conversion of thrombin into an anticoagulant by protein engineering, Nature. Nov. 23, 1995;378(6555):413-6.
Dibella, et al., Expression and folding of recombinant bovine prethrombin-2 and its activation to thrombin; J Biol Chem. Jan. 6, 1995;270(1):163-9.
Tsiang, et al., Protein engineering thrombin for optimal specificity and potency of anticoagulant activity in vivo., Biochemistry. Dec. 24, 1996;35(51):16449-57.
Leung, et al., Modulation of thrombin's procoagulant and anticoagulant properties.; Thromb Haemost. Jul. 1997;78 (1):577-80.
Carter, et al., Crystal structure of anticoagulant thrombin variant E217K provides insights into thrombin allostery; J Biol Chem. Jun. 18, 2004;279(25):26387-94. Epub Apr. 9, 2004.
Pineda, et al., The anticoagulant thrombin mutant W215A/E217A has a collapsed primary specificity pocket.J Biol Chem. Sep. 17, 2004;279(38):39824-8. Epub Jul. 13, 2004.
Tanaka, et al, Interaction between thrombin mutant W215A/E217A and direct thrombin inhibitor, Blood Coagul Fibrinolysis. Jul. 2008;19(5):465-8.
Gandhi, et al., Mechanism of the anticoagulant activity of thrombin mutant W215A/E217A; J Biol Chem. Sep. 4, 2009;284(36):24098-105.
Berny, et al., Thrombin mutant W215A/E217A treatment improves neurological outcome and reduces cerebral infarct size in a mouse model of ischemic stroke; Stroke. Jun. 2011;42(6):1736-41.
Banez, et al., Laboratory monitoring of heparin therapy—the effect of different salts of heparin on the activated partial thromboplastin time; Am J Clin Pathol. Oct. 1980;74(4 Suppl):569-74.
Bode, et al., The refined 1.9-A X-ray crystal structure of D-Phe-Pro-Arg chloromethylketone-inhibited human alpha-thrombin: structure analysis, overall structure, electrostatic properties, detailed active-site geometry, and structure-function relationships; Protein Sci. Apr. 1992;1(4):426-71.
Dang, et al., Rational engineering of activity and specificity in a serine protease; (1997) Nat. Biotechnol. 15:146-149.
Dang, et al., Selective Loss of Fibrinogen Clotting in a Loop-less Thrombin*; (1997) J. Biol. Chem. 272:19649-19651.
Stubbs, et al, A Player of Many Parts: The Spotlight Falls on Thrombin'S Structure; (1993) Thromb. Res., 69:1-58.
Rhee, et al., Role of Meizothrombin and Meizothrombin-(des F 1) in the Conversion of Prothrombin to Thrombin by the *Echis carinatus* Venom Coagulantt (1982) Biochemistry, 21:3437-3443.
Nishida, et al., cDNA Cloning and Deduced Amino Acid .Sequence of Prothrombin Activator (Ecarin) from Kenyan *Echis carinatus* Venom;(1995) Biochemistry, 34:1771-1778.
Naski, et al., The COOH-terminal Domain of Hirudin an Exosite-Directed Competitive Inhibitor of the Action of a-Thrombin on Fibrinogen; (1990) J. Biol. Chem., 265:13484-13489.
Naski, et al., A Kinetic Model for the a-Thrombin-catalyzed Conversion of Plasma Levels of Fibrinogen to Fibrin in the Presence of Antithrombin III*; (1991) J. Biol. Chem., 266:13003-13010.
Le Bonniec, et al., The Role of Thrombin's Tyr-Pro-Pro-Trp motif in the Interaction with Fibrinogen, Thrombomodulin, Protein C, Antithrombin III, and the Kunitz Inhibitors; (1993) J. Biol. Chem., 268:19055-19061.
Le Bonniec, et al., Interaction of Thrombin des-ETW with Antithrombin III, the Kunitz Inhibitors, Thrombomodulin and Protein C; (1992) J. Biol. Chem., 267:19341-19348.
Kawasaki, et al., Electron iilicroscopic Evnlutlfzn of Vat Morphology During Thrombelastography; (2004) Anesthesia & Analgesia, 99:1440-1444.
Gan, et al., Identification of Bask ino Acid Residues in Thrombin Essential for Heparin-catalyzed Inactivation by Antithrombin III*; (1994) J. Biol. Chem., 269:1301-1305.
Grinnell, Tipping the balance of blood coagulation, (1997) Nat. Biotechnol. 15124-125.
Morita, et al., Purification and Properties of Prothrombin Activator from the Venom of *Echis carinatusl*(1978), J. Biochem. 83:559-570.
Busch, et al., Thromboprophylaxis and Early Antithrombotic Therapy in Patients With Acute Ischemic Stroke and Cerebral Venous and Sinus Thrombosis (Apr. 30, 2004) Eur. J. Med. Res. 9:199-206.
Padma, Thrombolytic therapy for acute ischemic stroke: 3 h and beyond; (2005) Exp. Rev. Neurother. 5:223-233.
Bode, et al. The refined 1.9 A crystal structure of human a-thrombin: interaction with D-Phe-Pro-Arg chloromethyfttone and significance of the Tyr-Pro-Pro-Trp insertion segment (1989) EMBO J., 8:3467-3475.
Van Den Besselaar et al. Monitoring Heparin Therapy: Relationships between the Activated Partial Thromboplastin Time and Heparin Assays Based on Ex-Vivo Heparin Samples; (1990) Thrombosis and Haemostasis, 63:16-23.
Di Cera, Anticoagulant thrombins; Trends Cardiovasc Med. Nov. 1998;8(8):340-50.
Griffin, The thrombin paradox, Nature 378, 337-338 (Nov. 23, 1995).
GenBank entry P00734, retrieved from http://www.ncbi.nlm.nlh.gov/protein/p00734 on Jan. 8, 2014, Jan. 1, 1990.

* cited by examiner

EXPRESSION OF THROMBIN VARIANTS

CROSS REFERENCE TO RELATED APPLICATIONS

The present invention claims priority to U.S. Provisional Patent Ser. No. 61/426,385, filed on Dec. 22, 2010, entitled Expression of Anticoagulant Thrombin Mutants in *Escherichia coli*, whose disclosures are incorporated herein by reference.

GOVERNMENTAL SUPPORT

The present invention was made with governmental support pursuant to the following grants HL049413, HL058141, HL073813 and HL095315 awarded by National Institutes of Health. The government has certain rights in the invention.

BACKGROUND OF THE INVENTION

Although substantial progress has been made in the prevention and treatment of cardiovascular disease and its major risk factors, it has been predicted that thrombotic complications will remain the leading cause of death and disability and will represent a major burden to productivity worldwide well into the year 2020 [Gerszten, (2008) *Nature* 451:949-952]. Indeed, thrombosis is the most prevalent cause of fatal diseases in developed countries. It would be beneficial to have an antithrombotic agent that can be administered to patients with severe acute thrombotic diseases without the risk of causing hemorrhage, as experienced with antithrombotic/thrombolytic therapy in the treatment of acute ischemic stroke [Padma, (2005) *Exp. Rev. Neurother.* 5:223-233] or systemic anticoagulants like heparin [Busch, (2004) *Eur. J. Med. Res.* 9:199-206].

The gene for prothrombin encodes a protein referred to as preprothrombin [UniProtKB sequence P00734; SEQ ID NO:3] that contains 622 amino acid residues composed of several distinct domains. The first domain is a 43 amino acid residue leader sequence that is comprised of a signal peptide sequence and a propeptide. Cleavage of the leader sequence provides prothrombin that is comprised of Fragment-1 (residues 44-198), Fragment-2 (residues 199-327), and a fragment that contains the residues of the thrombin A-chain (residues 328-363) and the thrombin B-chain (residues 364-622). The portion containing Fragment-2, and thrombin (residues 199-622) is referred to as prethrombin-1.

When expressed in vivo, prothrombin can be cleaved by the prothrombinase complex between residues Arg271 and Thr272 (henceforth, the prothrombin numbering system is used unless otherwise specified) into a portion containing Fragment-1 and Fragment-2, and the prethrombin-2 fragment. Cleavage of prethrombin-2 between residues Arg320 and Ile321 and also between residues Arg284 and Thr285 forms thrombin. This last cleavage can be carried out by thrombin itself. Three letter code for amino acid residues is usually used herein for the identification of single amino acid residues. Single letter code is frequently used to identify two or more residues such as the Ala-substituted Trp and Glu residues of WE thrombin [see, Cantwell, (2000) *J. Biol. Chem.* 275:39827-39830]. Prothrombin can also be first cleaved between residues Arg320 and Ile321 to form meizothrombin, and thereafter between residues Arg271 and Thr272 and between residues Arg284 and Thr285 to form thrombin.

Alternatively, the enzyme ecarin can be used to cleave prothrombin between residues Arg271 and Thr272 to form meizothrombin. Autocatalytic processing results in the formation of meizothrombin desF1 and then thrombin. Rhee et al. (1982) *Biochemistry,* 21:3437-3443.

Ecarin is a snake venom-derived protease isolated from *Echis carinatus* [Morita et al., (1978), *J. Biochem.* 83:559-570]. A cDNA encoding ecarin has been cloned by Nishida et al., (1995) *Biochemistry,* 34:1771-1778].

Ecarin, a glycoprotein, is a metalloprotease, a mature form of which has 426 amino acid residues in total, having a mosaic structure comprising a $Zn^{2+}$ chelate, a disintegrin domain and a Cys-rich domain. Ecarin cleaves proteins and peptides after the sequence Asp-Gly-Arg or Glu-Gly-Arg. Ecarin has been used to cleave prothrombin between residues Arg320 and Ile321 to separate the A and B chains. U.S. Pat. No. 6,413,737.

Wild-type (wt) thrombin expressed from mammalian cells is often used for its procoagulant properties, particularly for the problem of surgical bleeding. Thrombin variants engineered for optimal activity toward protein C and minimal activity toward fibrinogen and protease-activated receptor 1 (PAR 1) have shown remarkable anticoagulant properties of therapeutic interest both in vitro and in vivo [Cantwell, (2000) *J. Biol. Chem.* 275:39827-39830; Gibbs, (1995) *Nature* 378:413-416; Dang, Guinto, (1997) *Nat. Biotechnol.* 15:146-149; Gruber, (2002) *J. Biol. Chem.* 277:27581-27584; Gruber, (2006) *J. Thromb. Haemost.* 4:392-397; Gruber, (2007) *Blood* 109:3733-3740; Tsiang, (1996) *Biochemstry* 35:16449-16457; Dang, (1997) *J. Biol. Chem.* 272:19649-19651; Griffin, (1195) *Nature* 378:337-338; Grinnell, (1997) *Nat. Biotechnol.* 15124-125].

The double mutant referred to as W215A/E217A (WE) is constructed by combining the two single mutations W215A and E217A in the thrombin molecule [Cantwell, (2000) *J. Biol. Chem.* 275:39827-39830]. W215A and E217A refer to amino acid residue positions in the thrombin amino acid residue sequence using the position numbers as described in Bode et al. (1989) *EMBO. J.,* 8:3467-3475, that correspond to sequential amino acid residue positions 263 and 265 from the N-terminus of thrombin, respectively. A correlation table is provided hereinafter.

WE thrombin exhibits anticoagulant/antithrombotic activity both in vitro and in vivo [Arosio, (2000) *Biochemistry* 39:8095-8101; Cantwell, (2000) *J. Biol. Chem.* 275, 39827-39830; Berny, (2008) *Arterioscler, Thromb. Vasc. Biol.* 18:329-334; Feistritzer, (2006) *J. Biol. Chem.* 281:20077-20084; Gruber, (2002) *J. Biol. Chem.* 277:27581-27584; Gruber, (2006) *J. Thromb. Haemost.* 4:392-397; Gruber, (2007) *Blood* 109, 3733-3740]. Its antithrombotic effect in non-human primates is more efficacious than the direct administration of activated protein C, and is safer to use than the administration of low molecular weight heparins [Gruber, (2007) *Blood* 109:3733-3740].

Activated protein C generated in situ with the mutant WE thrombin offers cytoprotective advantages over activated protein C administered to the circulation [Feistritzer, (2006) *J. Biol. Chem.* 281:20077-20084]. Furthermore, WE thrombin acts as a potent and safe antithrombotic by blocking the interaction of von Willebrand Factor with the platelet receptor GpIb [Berny, (2008) *Arterioscler, Thromb. Vasc. Biol.* 18:329-334; Gruber, (2007) *Blood* 109:3733-3740]. These properties of WE thrombin provide proof of principle that a thrombin mutant with preferential activity toward protein C would be a compelling anticoagulant/antithrombotic agent in vivo. [Marino, (2010) *J. Biol. Chem.* 285:19145-19152].

Recombinant human coagulation enzymes, in particular WE, have been expressed and produced in animal cell cultures. Maintenance and propagation of animal cell lines is complicated and expensive. Because thrombin mutants for therapeutic use are being developed, the need has emerged to produce these recombinant proteins in large quantities at an affordable cost. Previously, thrombin was being produced in animal cells, namely baby hamster kidney cells. As animal cell cultures and lines can be expensive, an alternative is needed. The discussion below illustrates an alternative expression technique that results in unexpected properties of the anticoagulant thrombin mutant WE.

BRIEF SUMMARY OF THE INVENTION

The present invention, in one aspect, contemplates a bacteria-derived (or -expressed) new recombinant E-WE thrombin enzyme precursor such as E-WE preprothrombin, E-WE prothrombin, E-WE prethrombin-1, E-WE prethrombin-2 and E-WE meizothrombin that contain the SEQ ID NO:1 amino acid residue sequence and are preferably *Escherichia coli* culture-derived or -expressed (*E. coli*-derived; or *E. coli*-expressed). A contemplated E-WE construct contains the SEQ ID NO:1 amino acid residue sequence, and preferably contains the SEQ ID NO: 5 amino acid residue sequence. A bacterially-expressed, glycosylation-free E-WE thrombin is also contemplated that contains the SEQ ID NO:1 amino acid residue sequence.

It has unexpectedly been discovered that a recombinant E-WE thrombin prepared from a bacteria-expressed precursor is surprisingly safer and has a greater anticoagulant (antithrombotic) therapeutic effect than a glycosylated WE thrombin expressed in a mammalian cell line from the same DNA coding sequence.

In another aspect, the invention also contemplates a thrombin precursor variant that can be activated by ecarin alone. Such a precursor variant preferably has an amino acid residue sequence of up to 622 residues that includes the amino acid residue sequence Asp/Glu-Gly-Arg; i.e., one of Asp or Glu peptide-bonded to Gly-Arg, (D/EGR), that is itself peptide-bonded to the N-terminal residue of the thrombin variant that is produced; that is the incipient N-terminal residue of the thrombin A chain or the residue that becomes the new N-terminal residue of the A chain; i.e., Thr285.

Where the thrombin variant produced is human wild-type thrombin or a E-WE thrombin as disclosed herein, those D/EGR residues are preferably located right before Thr 285, at the positions 282, 283 and 284 of the construct (see, for example, SEQ ID NOs: 4, 5, 6, 7, 8, 16, 17, 20, 21 and 22). This provides a wild-type or E-WE construct that can be cleaved (activated) using only ecarin. A most preferred E-WE precursor is the ecarin-only cleavable prethrombin-2 polypeptide of SEQ ID NO:5.

Thus, one aspect of the invention contemplates a glycosylation-free recombinant precursor of E-WE thrombin such as a E-WE preprothrombin, a E-WE meizothrombin, a E-WE prothrombin, a E-WE prethrombin-1, or a E-WE prethrombin-2 polypeptide that contains a tri-peptide, D/EGR, (ecarin cleavage site) sequence at positions 326, 327 and 328 relative to the N-terminus of the preprothrombin polypeptide of SEQ ID NO: 4, or positions 282, 283 and 284 of the prothrombin polypeptide SEQ ID NO: 19. A particularly preferred recombinant E-WE precursor such as a preprothrombin, E-WE meizothrombin, E-WE prothrombin and E-WE prethrombin-2 is expressed in *Escherichia coli* that is referred to herein as *Escherichia coli*-derived or -expressed (*E. coli*-derived or *E. coli*-expressed).

It should be understood that an *E. coli*-derived E-WE meizothrombin is formed by expression in *E. coli* followed by a post expression cleavage reaction that forms the A and B chains. However, *E. coli*-derived E-WE meizothrombin is nonetheless referred to together with a single chained precursor such as E-WE preprothrombin, E-WE prothrombin, E-WE prethrombin-1, and E-WE prethrombin-2 for ease of expression.

It is also noted that a "zymogen" by many usual definitions is an inactive enzyme precursor that has to be acted upon to form the active enzyme. Meizothrombins have some of the enzymatic activity of thrombin, but are also further acted upon to form thrombin. As such, meizothrombin, meizothrombin (des 1) an A-chain-shortened meizothrombin, and similar thrombin precursor compounds that have enzymatic activity, but must be acted upon to form thrombin are deemed active precursors of thrombin herein.

The E-WE thrombin produced by activation of one of the above zymogens or proteolytic processing of active precursors is also particularly preferred. It is believed that the enhanced antithrombotic activity and safety observed for a contemplated E-WE thrombin results from the completeness of the cleavage reaction provided by the use of only ecarin that permits a prepared E-WE thrombin to be substantially homogeneous and free from the presence of a N-terminally extended polypeptide in the thrombin A chain.

One contemplated bacteria-derived E-WE precursor includes the amino acid residue sequence of SEQ ID NO:1. A contemplated E-WE thrombin contains two chains, and also contains the amino acid residue sequence of SEQ ID NO:1. It is to be understood that E-WE thrombin contains a shorter (A chain) and longer (B chain) polypeptide linked together by a cystine bond, and that that sequence is read N-terminus to C-terminus as if the two polypeptides were one single chain, starting with the shorter A chain and followed by the longer B chain.

The terms "E-WE thrombin enzyme", "recombinant E-WE thrombin enzyme", and "E-WE thrombin" are often used herein as a short-hand phrase to encompass a contemplated glycosyl group-free E-WE thrombin enzyme having the human thrombin amino acid residue sequence in two chains and containing the B chain alanine for tryptophan (W) and alanine for glutamic acid (E) residue substitutions at positions 215 and 217 of the thrombin, respectively, using the position numbers as described in Bode et al. (1989) *EMBO. J.,* 8:3467-3475, that correspond to sequential amino acid residue positions 263 and 265 from the N-terminus of thrombin, respectively.

A E-WE thrombin is a preferred polypeptide. Because a E-WE thrombin enzyme is a two-chain polypeptide and cannot be prepared from a single polypeptide chain without post expression processing, it is to be understood that a polynucleotide encoding each of the E-WE ecarin site-containing precursors such as E-WE preprothrombin, E-WE prothrombin, E-WE meizothrombin, E-WE prethrombin-1, and E-WE prethrombin-2 polypeptides can be used to express a polypeptide that can itself be further processed with ecarin to provide a contemplated E-WE thrombin enzyme as an active agent for use in a contemplated composition and/or method. In some aspects, a precursor that contains an ecarin cleavage site peptide sequence bonded to the incipient thrombin A chain residue can be expressed in an eukaryotic cell such as a mammalian cell, an insect cell, a plant cell or a yeast cell, or in a bacterial cell such as an *E. coli* cell.

Specifically contemplated is a E-WE precursor (such as E-WE preprothrombin, E-WE prothrombin, E-WE meizothrombin, E-WE prethrombin-1, or E-WE prethrombin-2) mutant expressed in *E. coli*. Such a specifically contemplated E-WE precursor includes the amino acid residue sequence of SEQ ID NO:1, and preferably contains the amino acid residue sequence of SEQ ID NO: 5 as discussed elsewhere herein.

Yet another aspect of the invention contemplates a pharmaceutical composition that comprises an antithrombotic effective amount of a bacteria-expressed recombinant E-WE thrombin dissolved or dispersed in a pharmaceutically acceptable carrier. In one embodiment, a contemplated composition is adapted to be administered parenterally. One such contemplated carrier is an isotonic aqueous buffer.

A contemplated composition is intended for therapeutic use for enhancing hemostasis or treating and preventing thrombosis. An illustrative treatment comprises administering an above composition of an above-described E. coli-derived recombinant E-WE thrombin enzyme to a mammal in need thereof. It is contemplated that the administration is repeated a plurality of times.

Definitions

The term "anticoagulant" as used herein refers to any agent or agents capable of preventing or delaying blood clot formation in vitro and/or in vivo. The term "coagulation" as used herein refers to the process of polymerization of fibrin monomers, resulting in the transformation of blood or plasma from a liquid to a gel phase. Coagulation of liquid blood can occur in vitro, intravascularly or at an exposed and injured tissue surface. In vitro blood coagulation results in a gelled blood that maintains the cellular and other blood components in essentially the same relative proportions as found in non-coagulated blood, except for a reduction in fibrinogen content and a corresponding increase in fibrin. By "blood clot" is intended a viscous gel formed of, and containing all, components of blood in the same relative proportions as found in liquid blood.

Thrombin is a serine endopeptidase (EC 3.4.21.5) that cleaves the Arg-Gly bond in fibrinogen to form fibrin. Human thrombin is naturally made in the body from a precursor polypeptide referred to herein as preprothrombin that contains a single strand of 622 amino acid residues. Cleavage of that preprothrombin provides prothrombin, that contains a sequence of C-terminal 579 amino acid residues (subject to potential allelic variation or N-terminal microheterogeneity), plus the previous N-terminal pre-sequence of 43 residues that includes a signal peptide of 24 residues at its N-terminus, and a propeptide of 19 residues bonded to the C-terminus of the signal peptide [Degen et al. (1993) *Biochemistry* 22:2087-2097].

Prothrombin is a zymogen, or inactive protease, that is activated by a series of proteolytic cleavages to form thrombin. Prothrombin also contains the disulfide bond that is present in thrombin and links the two thrombin chains together. At least three sites in prothrombin are normally subject to cleavage.

In vivo, prothrombin is cleaved between residues Arg271 and Thr272 [residue numbers as described in Degen et al. (1993) *Biochemistry* 22:2087-2097] (sequentially, preprothrombin Arg327-Thr328) by coagulation Factor Xa (EC 3.4.21.6) another serine endopeptidase in the presence of Factor Va, phospholipid and calcium ions to yield prethrombin-2 and Fragment 1.2. The Fragment 1.2 polypeptide can also be cleaved to form Fragment 1 and Fragment 2. The prethrombin-2 fragment is cleaved as discussed below to provide thrombin.

The prethrombin-2 polypeptide is the smallest naturally-occurring single-chain immediate precursor of thrombin (corresponding to residues Thr272 to Glu579 in prothrombin), has one glycosylation site at Asn373 and four disulfide bonds, Cys293-Cys439, Cys348-Cys364, Cys493-Cys507, and Cys521-Cys551. The Cys293-Cys439 disulfide bond links the thrombin A chain (residues 272-320) and B chain (residues 321-579).

Prothrombin can also be proteolytically cleaved by the same enzyme system between residues Arg320 and Ile321 (preprothrombin Arg363-Ile364) to yield meizothrombin, which in turn cleaves autolytically between Arg155 and Ser156 (preprothrombin Arg198-Ser199) to produce Fragment 1 (prothrombin 1-155; preprothrombin Ala43-Arg198) and meizothrombin des 1 [a disulfide-linked dipeptide extending from original prothrombin residue 156 (preprothrombin precursor Ser199) to the carboxy-terminus of prothrombin].

Finally, thrombin is made from prethrombin-2 by further reaction with Factor Xa in the presence of Factor Va, phospholipid and calcium ions, this time to cleave between residues Arg320 and Ile321 (preprothrombin Arg363-Ile364, or prothrombin, Arg328 and Ile329) and between residues Arg284 and Thr285. Thrombin can also be formed from meizothrombin des 1 by proteolytic cleavage between Arg271 and Thr272 (prothrombin Arg271 and Thr272). Cleavage between preprothrombin residues Arg363 and Ile364 (prothrombin Arg320 and Ile321) forms the mature thrombin having a disulfide-bonded 36-residue light chain and 259-residue heavy chain.

The term "thrombin" as used herein refers to a multifunctional enzyme that contains up to about 300 residues in two polypeptide chains connected by a disulfide bond that exhibits at least two of the activities exemplified in Table 3, hereinafter. Thrombin can act as a procoagulant by the proteolytic cleavage of fibrinogen to fibrin. Thrombin can also activate the clotting Factors V (FV), VIII (FVIII), XI (FXI) and XIII (FXIII) leading to perpetuation of clotting, and the cleavage of the platelet thrombin receptor, PAR-1, leading to platelet activation. Thrombin can also activate protein C.

Multiple antithrombotic mechanisms limit thrombin generation and activity. When thrombin binds to thrombomodulin (TM), an integral membrane protein on vascular endothelial cells, thrombin undergoes a conformational change and loses its procoagulant activity. Thrombin then acquires the ability to convert the zymogen protein C (PC) to activated protein C (APC). APC, another serine endopeptidase (EC 3.4.21.69), acts as a potent anticoagulant by inactivating activated FV (FVa) and FVIII (FVIIIa), two essential cofactors in the clotting or coagulation cascade. APC also inactivates plasminogen activator inhibitor-1 (PAI-1), the major physiologic inhibitor of tissue plasminogen activator (tPA), thus potentiating normal fibrinolysis.

The term "coagulation cascade" as used herein refers to three interconnecting enzyme pathways as described, for example, by Manolin in Wilson et al. (eds): *Harrison's Principle of Internal Medicine,* 14.sup.th Ed. New York. McGraw-Mill, 1998, p. 341, incorporated herein by reference in its entirety. The intrinsic coagulation pathway leads to the formation of Factor IXa, that in conjunction with Factors VIIIa and X, phospholipid and $Ca^{2+}$ provides Factor Xa. The extrinsic pathway provides Factor Xa and IXa after the combination of tissue factor and Factor VII. The common coagulation pathway interacts with the blood coagulation Factors V, VIII, IX and X to cleave prothrombin to thrombin (Factor IIa), which is then able to cleave fibrinogen to fibrin.

At least two distinct amino acid numbering systems are in use for thrombin in addition to the DNA-based system of Degen et al. [Degen et al. (1993) *Biochemistry,* 22:2087-2097.] One is based on alignment with chymotrypsinogen as described by Bode et al. and is the numbering system used most widely in the protease field [Bode et al. (1989) *EMBO.*

J., 8:3467-3475]. In a second system, the Sadler numbering scheme, the B chain of thrombin commences with Ile1 and extends to Glu259, whereas the A chain is designated with "a" postscripts, as in Thr1a to Arg36a.

For example, Wu et al. have disclosed several thrombin mutants numbered in accordance with the Sadler scheme [Wu et al. (1991) *Proc. Natl. Acad. Sci. U.S.A.*, 88:6775-6779]. The Wu et al. mutants and the corresponding chymotrypsinogen and Degen et al. residue numbers, respectively, are sequentially shown as follows: His43 (57, 363), Lys52 (60f, 372), Asn53 (60 g, 373), Arg62 (67, 382), Arg68 (73, 388), Arg70 (75, 390), Asp99 (102, 419) and Ser205 (195, 525).

Throughout the present specification, the Bode et al. numbering system is recited first to refer to amino acid residues for thrombin and thrombin mutants, and is often followed by a sequential numbering based on the preprothrombin or prothrombin numbering. However, for the sequence listings corresponding to human recombinant thrombin enzyme mutant W215A/E217A (E-WE; SEQ ID NO:1), and wild type (WT) human thrombin (SEQ ID NO:2), a sequential numbering system is used. A third numbering system based on the preprothrombin sequence of SEQ ID NO: 4 is also sometimes used, particularly when a polypeptide longer than thrombin is discussed.

Accordingly, amino acid positions 215 and 217 of thrombin and the E-WE thrombin enzyme as described in the present specification using the Bode et al. system correspond to amino acid positions 263 and 265 of E-WE thrombin mutants and wild type thrombin in the sequential numbering system used in SEQ ID NOS:1 and 2. Those positions correspond to position numbers 547 and 549 of the prothrombin sequence and to 590 and 592 of the preprothrombin sequence of SEQ ID NOs:3 or 4.

A side-by-side comparison of the amino acid sequence for WT thrombin (prethrombin-2) using the Bode et al. sequential numbering system vs. the system used in SEQ ID NOS:1 and 2 is provided in Table A, below. As listed in Table A, the thrombin A-chain starts at amino acid residue number 1 of the sequential numbering system, whereas the thrombin B-chain starts at amino acid residue number 37.

TABLE A

Sequential and Bode et al. Numbering for the Amino Acid Residue Sequence of Wild Type Human Thrombin of SEQ ID NO: 2

| Sequential Number | Bode et al. Number | Amino Acid Residue | Preprothrombin Number |
|---|---|---|---|
| 1 | 1h | THR | 328 |
| 2 | 1g | PHE | 329 |
| 3 | 1f | GLY | 330 |
| 4 | 1e | SER | 331 |
| 5 | 1d | GLY | 332 |
| 6 | 1c | GLU | 333 |
| 7 | 1b | ALA | 334 |
| 8 | 1a | ASP | 335 |
| 9 | 1 | CYS | 336 |
| 10 | 2 | GLY | 337 |
| 11 | 3 | LEU | 338 |
| 12 | 4 | ARG | 339 |
| 13 | 5 | PRO | 340 |
| 14 | 6 | LEU | 341 |
| 15 | 7 | PHE | 342 |
| 16 | 8 | GLU | 343 |
| 17 | 9 | LYS | 344 |
| 18 | 10 | LYS | 345 |
| 19 | 11 | SER | 346 |
| 20 | 12 | LEU | 347 |
| 21 | 13 | GLU | 348 |
| 22 | 14 | ASP | 349 |
| 23 | 14a | LYS | 350 |
| 24 | 14b | THR | 351 |
| 25 | 14c | GLU | 352 |
| 26 | 14d | ARG | 353 |
| 27 | 14e | GLU | 354 |
| 28 | 14f | LEU | 355 |
| 29 | 14g | LEU | 356 |
| 30 | 14h | GLU | 357 |
| 31 | 14i | SER | 358 |
| 32 | 14j | TYR | 359 |
| 33 | 14k | ILE | 360 |
| 34 | 14l | ASP | 361 |
| 35 | 14m | GLY | 362 |
| 36 | 15 | ARG | 363 |
| 37 | 16 | ILE | 364 |
| 38 | 17 | VAL | 365 |
| 39 | 18 | GLU | 366 |
| 40 | 19 | GLY | 367 |
| 41 | 20 | SER | 368 |
| 42 | 21 | ASP | 369 |
| 43 | 22 | ALA | 370 |
| 44 | 23 | GLU | 371 |
| 45 | 24 | ILE | 372 |
| 46 | 25 | GLY | 373 |
| 47 | 26 | MET | 374 |
| 48 | 27 | SER | 375 |

TABLE A-continued

Sequential and Bode et al. Numbering for
the Amino Acid Residue Sequence of Wild
Type Human Thrombin of SEQ ID NO: 2

| Sequential Number | Bode et al. Number | Amino Acid Residue | Preprothrombin Number |
|---|---|---|---|
| 49 | 28 | PRO | 376 |
| 50 | 29 | TRP | 377 |
| 51 | 30 | GLN | 378 |
| 52 | 31 | VAL | 379 |
| 53 | 32 | MET | 380 |
| 54 | 33 | LEU | 381 |
| 55 | 34 | PHE | 382 |
| 56 | 35 | ARG | 383 |
| 57 | 36 | LYS | 384 |
| 58 | 36a | SER | 385 |
| 59 | 37 | PRO | 386 |
| 60 | 38 | GLN | 387 |
| 61 | 39 | GLU | 388 |
| 62 | 40 | LEU | 389 |
| 63 | 41 | LEU | 390 |
| 64 | 42 | CYS | 391 |
| 65 | 43 | GLY | 392 |
| 66 | 44 | ALA | 393 |
| 67 | 45 | SER | 394 |
| 68 | 46 | LEU | 395 |
| 69 | 47 | ILE | 396 |
| 70 | 48 | SER | 397 |
| 71 | 49 | ASP | 398 |
| 72 | 50 | ARG | 399 |
| 73 | 51 | TRP | 400 |
| 74 | 52 | VAL | 401 |
| 75 | 53 | LEU | 402 |
| 76 | 54 | THR | 403 |
| 77 | 55 | ALA | 404 |
| 78 | 56 | ALA | 405 |
| 79 | 57 | HIS | 4406 |
| 80 | 58 | CYS | 407 |
| 81 | 59 | LEU | 408 |
| 82 | 60 | LEU | 409 |
| 83 | 60a | TYR | 410 |
| 84 | 60b | PRO | 411 |
| 85 | 60c | PRO | 412 |
| 86 | 60d | TRP | 413 |
| 87 | 60e | ASP | 414 |
| 88 | 60f | LYS | 415 |
| 89 | 60g | ASN | 416 |
| 90 | 60h | PHE | 417 |
| 91 | 60i | THR | 418 |
| 92 | 61 | GLU | 419 |
| 93 | 62 | ASN | 420 |
| 94 | 63 | ASP | 421 |
| 95 | 64 | LEU | 422 |
| 96 | 65 | LEU | 423 |
| 97 | 66 | VAL | 424 |
| 98 | 67 | ARG | 425 |
| 99 | 68 | ILE | 426 |
| 100 | 69 | GLY | 427 |
| 101 | 70 | LYS | 428 |
| 102 | 71 | HIS | 429 |
| 103 | 72 | SER | 430 |
| 104 | 73 | ARG | 431 |
| 105 | 74 | THR | 432 |
| 106 | 75 | ARG | 433 |
| 107 | 76 | TYR | 434 |
| 108 | 77 | GLU | 435 |
| 109 | 77a | ARG | 436 |
| 110 | 78 | ASN | 437 |
| 111 | 79 | ILE | 438 |
| 112 | 80 | GLU | 439 |
| 113 | 81 | LYS | 440 |
| 114 | 82 | ILE | 441 |
| 115 | 83 | SER | 442 |
| 116 | 84 | MET | 443 |
| 117 | 85 | LEU | 444 |
| 118 | 86 | GLU | 445 |
| 119 | 87 | LYS | 446 |
| 120 | 88 | ILE | 447 |
| 121 | 89 | TYR | 448 |

TABLE A-continued

Sequential and Bode et al. Numbering for the Amino Acid Residue Sequence of Wild Type Human Thrombin of SEQ ID NO: 2

| Sequential Number | Bode et al. Number | Amino Acid Residue | Preprothrombin Number |
|---|---|---|---|
| 122 | 90 | ILE | 449 |
| 123 | 91 | HIS | 450 |
| 124 | 92 | PRO | 451 |
| 125 | 93 | ARG | 452 |
| 126 | 94 | TYR | 453 |
| 127 | 95 | ASN | 454 |
| 128 | 96 | TRP | 455 |
| 129 | 97 | ARG | 456 |
| 130 | 97a | GLU | 457 |
| 131 | 98 | ASN | 458 |
| 132 | 99 | LEU | 459 |
| 133 | 100 | ASP | 460 |
| 134 | 101 | ARG | 461 |
| 135 | 102 | ASP | 462 |
| 136 | 103 | ILE | 463 |
| 137 | 104 | ALA | 464 |
| 138 | 105 | LEU | 465 |
| 139 | 106 | MET | 466 |
| 140 | 107 | LYS | 467 |
| 141 | 108 | LEU | 468 |
| 142 | 109 | LYS | 469 |
| 143 | 110 | LYS | 470 |
| 144 | 111 | PRO | 471 |
| 145 | 112 | VAL | 472 |
| 146 | 113 | ALA | 473 |
| 147 | 114 | PHE | 474 |
| 148 | 115 | SER | 475 |
| 149 | 116 | ASP | 476 |
| 150 | 117 | TYR | 477 |
| 151 | 118 | ILE | 478 |
| 152 | 119 | HIS | 479 |
| 153 | 120 | PRO | 480 |
| 154 | 121 | VAL | 481 |
| 155 | 122 | CYS | 482 |
| 156 | 123 | LEU | 483 |
| 157 | 124 | PRO | 484 |
| 158 | 125 | ASP | 485 |
| 159 | 126 | ARG | 486 |
| 160 | 127 | GLU | 487 |
| 161 | 128 | THR | 488 |
| 162 | 129 | ALA | 489 |
| 163 | 129a | ALA | 490 |
| 164 | 129b | SER | 491 |
| 165 | 129c | LEU | 492 |
| 166 | 130 | LEU | 493 |
| 167 | 131 | GLN | 494 |
| 168 | 132 | ALA | 495 |
| 169 | 133 | GLY | 496 |
| 170 | 134 | TYR | 497 |
| 171 | 135 | LYS | 498 |
| 172 | 136 | GLY | 499 |
| 173 | 137 | ARG | 500 |
| 174 | 138 | VAL | 501 |
| 175 | 139 | THR | 502 |
| 176 | 140 | GLY | 503 |
| 177 | 141 | TRP | 504 |
| 178 | 142 | GLY | 505 |
| 179 | 143 | ASN | 506 |
| 180 | 144 | LEU | 507 |
| 181 | 145 | LYS | 508 |
| 182 | 146 | GLU | 509 |
| 183 | 147 | THR | 510 |
| 184 | 148 | TRP | 511 |
| 185 | 149 | THR | 512 |
| 186 | 149a | ALA | 513 |
| 187 | 149b | ASN | 514 |
| 188 | 149c | VAL | 515 |
| 189 | 149d | GLY | 516 |
| 190 | 149e | LYS | 517 |
| 191 | 150 | GLY | 518 |
| 192 | 151 | GLN | 519 |
| 193 | 152 | PRO | 520 |
| 194 | 153 | SER | 521 |

TABLE A-continued

Sequential and Bode et al. Numbering for the Amino Acid Residue Sequence of Wild Type Human Thrombin of SEQ ID NO: 2

| Sequential Number | Bode et al. Number | Amino Acid Residue | Preprothrombin Number |
|---|---|---|---|
| 195 | 154 | VAL | 522 |
| 196 | 155 | LEU | 523 |
| 197 | 156 | GLN | 524 |
| 198 | 157 | VAL | 525 |
| 199 | 158 | VAL | 526 |
| 200 | 159 | ASN | 527 |
| 201 | 160 | LEU | 528 |
| 202 | 161 | PRO | 529 |
| 203 | 162 | ILE | 530 |
| 204 | 163 | VAL | 531 |
| 205 | 164 | GLU | 532 |
| 206 | 165 | ARG | 533 |
| 207 | 166 | PRO | 534 |
| 208 | 167 | VAL | 535 |
| 209 | 168 | CYS | 536 |
| 210 | 169 | LYS | 537 |
| 211 | 170 | ASP | 538 |
| 212 | 171 | SER | 539 |
| 213 | 172 | THR | 540 |
| 214 | 173 | ARG | 541 |
| 215 | 174 | ILE | 542 |
| 216 | 175 | ARG | 543 |
| 217 | 176 | ILE | 544 |
| 218 | 177 | THR | 545 |
| 219 | 178 | ASP | 546 |
| 220 | 179 | ASN | 547 |
| 221 | 180 | MET | 548 |
| 222 | 181 | PHE | 549 |
| 223 | 182 | CYS | 550 |
| 224 | 183 | ALA | 551 |
| 225 | 184 | GLY | 552 |
| 226 | 184a | TYR | 553 |
| 227 | 185 | LYS | 554 |
| 228 | 186 | PRO | 555 |
| 229 | 186a | ASP | 556 |
| 230 | 186b | GLU | 557 |
| 231 | 186c | GLY | 558 |
| 232 | 186d | LYS | 559 |
| 233 | 187 | ARG | 560 |
| 234 | 188 | GLY | 561 |
| 235 | 189 | ASP | 562 |
| 236 | 190 | ALA | 563 |
| 237 | 191 | CYS | 564 |
| 238 | 192 | GLU | 565 |
| 239 | 193 | GLY | 566 |
| 240 | 94 | ASP | 567 |
| 241 | 195 | SER | 568 |
| 242 | 196 | GLY | 569 |
| 243 | 197 | GLY | 570 |
| 244 | 198 | PRO | 571 |
| 245 | 199 | PHE | 572 |
| 246 | 200 | VAL | 573 |
| 247 | 201 | MET | 574 |
| 248 | 202 | LYS | 575 |
| 249 | 203 | SER | 576 |
| 250 | 204 | PRO | 577 |
| 251 | 204a | PHE | 578 |
| 252 | 204b | ASN | 579 |
| 253 | 205 | ASN | 580 |
| 254 | 206 | ARG | 581 |
| 255 | 207 | TRP | 582 |
| 256 | 208 | TYR | 583 |
| 257 | 209 | GLN | 584 |
| 258 | 210 | MET | 585 |
| 259 | 211 | GLY | 586 |
| 260 | 212 | ILE | 587 |
| 261 | 213 | VAL | 588 |
| 262 | 214 | SER | 589 |
| 263 | 215 | TRP | 590 |
| 264 | 216 | GLY | 591 |
| 265 | 217 | GLU | 592 |
| 266 | 219 | GLY | 593 |
| 267 | 220 | CYS | 594 |

TABLE A-continued

Sequential and Bode et al. Numbering for the Amino Acid Residue Sequence of Wild Type Human Thrombin of SEQ ID NO: 2

| Sequential Number | Bode et al. Number | Amino Acid Residue | Preprothrombin Number |
|---|---|---|---|
| 268 | 221 | ASP | 595 |
| 269 | 221a | ARG | 596 |
| 270 | 222 | ASP | 597 |
| 271 | 223 | GLY | 598 |
| 272 | 224 | LYS | 599 |
| 273 | 225 | TYR | 600 |
| 274 | 226 | GLY | 601 |
| 275 | 227 | PHE | 602 |
| 276 | 228 | TYR | 603 |
| 277 | 229 | THR | 604 |
| 278 | 230 | HIS | 605 |
| 279 | 231 | VAL | 606 |
| 280 | 232 | PHE | 607 |
| 281 | 233 | ARG | 608 |
| 282 | 234 | LEU | 609 |
| 283 | 235 | LYS | 610 |
| 284 | 236 | LYS | 611 |
| 285 | 237 | TRP | 612 |
| 286 | 238 | ILE | 613 |
| 287 | 239 | GLN | 614 |
| 288 | 240 | LYS | 615 |
| 289 | 241 | VAL | 616 |
| 290 | 242 | ILE | 617 |
| 291 | 243 | ASP | 618 |
| 292 | 244 | GLN | 619 |
| 293 | 245 | PHE | 620 |
| 294 | 246 | GLY | 621 |
| 295 | 247 | GLU | 622 |

A contemplated E-WE precursor and E-WE thrombin has sequence identity to the amino acid residue sequence of a human thrombin that has alanine amino acid residue substitutions at residue positions 215 and 217 of thrombin of SEQ ID NO:2, as determined by sequence alignment programs and parameters described elsewhere herein. The thrombin portion of a contemplated recombinant E-WE thrombin precursor such as E-WE preprothrombin, E-WE prothrombin, E-WE meizothrombin, E-WE prethrombin-1, E-WE prethrombin-2 or E-WE thrombin has the amino acid residue sequence of SEQ ID NO:1, treating E-WE meizothrombin and E-WE thrombin as if they were each single chained molecules.

In one embodiment of the present invention, a E-WE preprothrombin, prothrombin, meizothrombin, E-WE prethrombin-1, prethrombin-2 or thrombin has both an active (catalytic) site and exosite I available for binding to direct thrombin inhibitors (DTIs). The active site cleft of thrombin is bordered by two prominent insertion loops (i.e., the 60-loop and the 148-loop) that control, in part, the interaction of substrates and inhibitors with the active site [Bode et al. (1989) *EMBO J.,* 8:3467-3475; Le Bonniec et al. (1993) *J. Biol. Chem.,* 268:19055-19061; Le Bonniec et al. (1992) *J. Biol. Chem.,* 267:19341-19348].

Exosites I and II are electropositive sites in near-opposition on the surface of thrombin known to bind to a number of substrates (Stubbs and Bode (1993) *Thromb. Res.,* 69:1-58; Bode et al. (1992) *Protein Sci.,* 1:26-471). For example, exosite I is known to bind fibrinogen and fibrin I and II (see, for example, Naski et al. (1990) *J. Biol. Chem.,* 265:13484-13489; Naski and Shafer (1991) *J. Biol. Chem.,* 266:13003-13010), whereas exosite II is known to bind heparin and other glycosaminoglycans (Bode et al. (1992) *Protein Sci.,* 1:26-471; Gan et al. (1994) *J. Biol. Chem.,* 269:1301-1305).

The term "procoagulant" as used herein refers to agents that initiate or accelerate the process of blood coagulation through the transformation of soluble circulating fibrinogen to an insoluble cross-linked, fibrin network. An exemplary procoagulant is native thrombin that proteolytically cleaves fibrinogen to fibrin. In vitro, the procoagulant ultimately yields a blood clot. In vivo, a procoagulant typically yields a thrombus under pathological conditions.

The term "thrombus" as used herein refers to a coagulated intravascular mass formed from the components of blood that results from a pathological condition of an animal or human. Typically, the constituents of a thrombus have relative proportions differing from those of the same components in circulating blood. A thrombus is generated in vivo by a dynamic process that comprises cleavage of fibrinogen to fibrin, activation of platelets and the adherence of platelets to the cross-linked fibrin network.

"Reduced procoagulant" or "anticoagulant" or "antithrombotic" activity, as used herein, can be determined for a E-WE thrombin through the calculation of its PA/FC ratio (also called "relative anticoagulant potency" or "RAP") [see, e.g., Di Cera (1998) *Trends Cardiovasc. Med.,* 8:340-350; Dang et al. (1997) *Nat. Biotechnol.,* 15:146-149]. The term "PA/FC ratio" refers to the ratio of the percent of wild-type protein C activation (PA) activity exhibited by a thrombin relative to the percent of wild-type fibrinogen clotting (FC) activity of that thrombin. A value of PA/FC greater than 1.0 indicates that the E-WE thrombin has reduced procoagulant fibrinogen cleavage activity relative to the residual antithrombotic activity resulting from protein C activation.

The present invention has several benefits and advantages.

One benefit is that the costly and time-consuming activation process requiring the use of Factor Xa in the presence of Factor Va, phospholipid and calcium ions is not required.

An advantage of the invention is that E-WE thrombin formation from a E-WE precursor that contains the 4 mutations relative to wt thrombin can be carried out in a single reaction using ecarin.

Another benefit of the invention is that the E-WE thrombin prepared from a contemplated E-WE precursor exhibits greater safety and antithrombotic activity than the glycosylated E-WE thrombin produced in a mammalian cell culture, whereas other thrombins produced in mammalian and bacterial cells had similar activities.

Another advantage of the present invention is that preparation of a E-WE precursor in bacterial culture lowers the possible risks of contamination with a mammalian pathogen or allergen.

A yet further benefit of the invention is that the production of E-WE thrombin is less costly using a contemplated E-WE precursor as a reactant and expression from bacteria instead of mammalian cells.

A still further benefit of the invention is that introduction of ecarin cleavage sites into the mutant E-WE thrombin precursor W215A/E217A/N282D/P283G that replaces the usual prothrombinase cleavage site located up-stream of and immediately adjacent to the incipient N-terminal residue of a mature thrombin molecule provides a new molecular entity and permits formation of the A chain N-terminal residue and the A and B chain cleavage using the same enzyme, which overcomes or minimizes the greatly reduced rate of Factor Xa-catalyzed cleavage of a E-WE precursor at that position.

A still further benefit of the invention is that introduction of an ecarin cleavage site into a precursor that replaces the Factor Xa site at prothrombin position 184 provides a new molecular entity and permits formation of the A chain N-terminal residue and the A and B chain cleavage using the same enzyme, which overcomes or minimizes the greatly reduced rate of Factor Xa-catalyzed cleavage of a E-WE precursor at that position.

Still further benefits and advantages will be apparent to a worker of ordinary skill from the detailed description that follows.

DETAILED DESCRIPTION OF THE INVENTION

One aspect of the present invention contemplates a bacteria-derived (-grown or -expressed) recombinant E-WE thrombin precursor such as E-WE preprothrombin, E-WE prothrombin, E-WE prethrombin-1, E-WE prethrombin-2 or E-WE meizothrombin that contains the SEQ ID NO:1 amino acid residue sequence and are preferably *Escherichia coli* culture-derived (or -expressed; *E. coli*-derived; *E. coli*-expressed). A contemplated E-WE precursor more preferably contains the SEQ ID NO: 5 amino acid residue sequence. A bacterially-expressed, glycosylation-free E-WE thrombin is also contemplated that contains the SEQ ID NO:1 amino acid residue sequence.

It has unexpectedly been discovered that an *E. coli*-derived recombinant E-WE thrombin enzyme is safer and has a greater antithrombotic therapeutic effect than its mammalian cell-expressed (-derived) analogue produced from the same DNA coding sequence. Therefore, a bacteria-derived E-WE thrombin enzyme is more useful than mammalian cell line-derived E-WE thrombin for the treatment and prevention of diseases that are associated with pathological blood coagulation.

A particular feature of bacterially-expressed polypeptides and proteins is that those expression products are non-glycosylated or glycosyl-free polypeptides and proteins. As a consequence, a contemplated to bacteria-derived (-expressed) E-WE thrombin or E-WE thrombin precursor can also be referred to as a non-glycosylated or glycosyl-free E-WE thrombin or E-WE thrombin precursor.

The present invention provides a recombinant E-WE thrombin enzyme, a composition and a method for inhibiting the effect of coagulants in vitro as well as in vivo. As discussed herein, E-WE precursors such as recombinant E-WE preprothrombin, E-WE prothrombin, E-WE meizothrombin, E-WE prethrombin-1, E-WE prethrombin-2, and E-WE thrombin are contemplated in which an alanine residue replaces each of a tryptophan and a glutamic acid residue at positions 215 and 217, respectively, in the thrombin sequence that is referred to as W215A/E217A or E-WE. These enzymes can be used in various applications to improve therapeutic efficacy and safety.

Also contemplated are a precursor that contains an ecarin cleavage site comprising the sequence Asp/Glu-Gly-Arg peptide-bonded to the incipient N-terminal residue of the thrombin A chain, that is, at residue positions 325-327 relative to the N-terminus of preprothrombin of SEQ ID NO:6. A contemplated thrombin precursor polypeptide preferably has an amino acid residue sequence of up to about 622 residues as in preprothrombin. It is preferred that the Asp/Glu-Gly-Arg sequence cleavage site be present 298-296 amino acid residues from the carboxy-terminus.

Four and five residue ecarin cleavage sites are also contemplated. Illustrative sites include the sequences Asp/Glu-Gly-Arg; Ile-Asp/Glu-Gly-Arg; Asp/Glu-Gly-Arg-Ile; Ile-Asp/Glu-Gly-Arg-Ile-Val (SEQ ID NO: 14); and Asp/Glu-Gly-Arg-Ile-Val-Glu (SEQ ID NO: 15), where in each case, the ecarin cuts after the Arg residue of the site.

In another aspect, a contemplated precursor polypeptide, except for the Asp/Glu-Gly-Arg sequence, contains the amino acid residue sequence of wild type human thrombin of SEQ ID NO:2. An illustrative precursor is that of sequence of SEQ ID NOs:6 or 7.

In another aspect of the invention, a precursor polypeptide containing an Asp/Glu-Gly-Arg sequence located as discussed above, is part of an amino acid residue sequence whose thrombin portion (the portion that forms thrombin) is at least about 95 percent identical to the amino acid residue sequence of wild type human thrombin of SEQ ID NO:2. More preferably, a thrombin portion is about 97 percent or more identical to that of wild type human thrombin of SEQ ID NO:2, most preferably, the identity is about 98 percent or more.

Illustrative non-wild type ecarin-cleavable thrombin precursors are those of sequence of SEQ ID NOs:4, 5, 8, 16 and 20. Another group of illustrative non-wild type thrombin precursors include the amino acid sequence of SEQ ID NOs: 1, 9 or 10.

Inasmuch as thrombin contains 295 amino acid residues, a contemplated thrombin portion can differ from wild type human thrombin of SEQ ID NO:2 by up to about 15 residues. A more preferred thrombin portion of a thrombin precursor can differ from wild type human thrombin of SEQ ID NO:2 by about nine amino acid residues. Illustratively, a thrombin precursor containing the Δ146-149e deletion of thrombin sequential positions 182-188 is missing seven thrombin residues and therefore differs from the thrombin of SEQ ID NO:2 by seven residues. A thrombin precursor containing sequence a W215G mutation along with the Δ146-149e deletion (W215G/A146-149e) differs from wild type human thrombin of SEQ ID NO:2 by eight amino acid residues, as does W215E/Δ146-149e. A E-WE thrombin precursor also containing a Δ146-149e deletion differs by nine residues.

In addition to thrombin and thrombin precursors containing the E-WE substitutions, the present invention provides a recombinant E-WE thrombin precursor (E-WE preprothrombin, E-WE prothrombin, E-WE meizothrombin, E-WE prethrombin-2) that also contains an added ecarin cleavage site at positions 325, 326 and 327 from the N-terminus of preprothrombin, where the site is Asp/Glu-Gly-Arg. A contemplated E-WE thrombin precursor has the sequence of SEQ ID NO: 4, and more preferably of the ecarin-cleavable pethrombin-2 polypeptide of SEQ ID NO:5.

It is also to be noted that a contemplated thrombin precursor need not be a well known thrombin precursor as discussed above. Rather, a contemplated thrombin precursor can be viewed as a expressible fusion protein (polypeptide) in which the N-terminal portion of the fusion polypeptide provides a convenient sequence for expression and/or purification (expression/purification), whose C-terminal residue is peptide-bonded to an ecarin cleavage sequence as discussed above, whose Arg residue is peptide-bonded to the carboxy-terminal portion that is the thrombin sequence desired to be expressed. Thus, the N-terminal portion of the expressed fusion polypeptide (protein) is a convenient expression/purification sequence, whereas the C-terminal portion has a desired thrombin sequence, and the two portions are joined (linked) by the amino acid residue sequence of an ecarin cleavage site.

Thus, an exemplary N-terminal fusion polypeptide portion can be a commonly expressed polypeptide such as FLAG peptide, β-galactosidase (β-Gal or LacZ), glutathione-S-transferase (GST) protein, a hexa-his peptide (6×His-tag), chitin binding protein (CBP), maltose binding protein (MBP), V5-tag, c-myc-tag, HA-tag, and the like as are well known. The carboxy-terminus of the N-terminal fusion polypeptide portion is peptide bonded to an ecarin cleavage site as discussed above and the Arg of that ecarin cleavage sequence is peptide-bonded to the incipient N-terminal residue of a desired thrombin sequence that constitutes the carboxy-terminal portion of the fusion protein or polypeptide.

An illustrative desired thrombin sequence is that of wild type human thrombin of SEQ ID NO:2, E-WE thrombin of SEQ ID NO:1, Δ146-149e thrombin and the like. Illustrative carboxy-terminal thrombin portions of such fusion polypeptides include the ecarin-activatable E-WE thrombin precursor A of SEQ ID NO:16 and the ecarin-activatable thrombin precursor A of SEQ ID NO:17. Further examples of sequences of a carboxy-terminal thrombin portion and the linking ecarin cleavage site for a E-WE thrombin and for a wild-type thrombin are illustrated by SEQ ID NOs: 21 and 22.

The present invention enables large scale production of a recombinant thrombin, a E-WE thrombin precursor, such as E-WE preprothrombin, E-WE prothrombin, E-WE meizothrombin, E-WE prethrombin-2 and thrombin enzyme W215A/E217A (E-WE) for in vitro and in vivo studies, therapies and other applications that are discussed herein. A contemplated bacterial expression product also preferably contains the ecarin cleavage site present in the SEQ ID NO:5 amino acid residue sequence. In addition, this type of large scale production is cost-effective compared to commonly used thrombin, meizothrombin, prethrombin-2 or prothrombin expression in baby hamster kidney (BHK) or other mammalian cells.

The invention also provides a form of E-WE thrombin enzyme that is significantly less active toward the procoagulant substrate fibrinogen than the BHK-expressed version. Moreover, a recombinant E-WE preprothrombin, E-WE prothrombin, E-WE meizothrombin, or E-WE prethrombin-2 expressed in E. coli provides a more potent anti-coagulant E-WE thrombin than the corresponding E-WE thrombin expressed in BHK cells, and therefore permits use of lower effective doses when used for the treatment of disease.

Wild type (WT) human thrombin and other anticoagulant mutants studied expressed in E. coli are not more potent than their BHK-expressed counterparts, but rather, have the same potency. Accordingly, an E. coli-derived recombinant E-WE thrombin enzyme and a E-WE thrombin precursor such as a E-WE meizothrombin, a E-WE prethrombin-2, a E-WE prothrombin, and a E-WE preprothrombin from which E-WE thrombin can be prepared, can be more useful therapeutically or in other uses than a BHK cell-derived E-WE thrombin, E-WE prethrombin-2, E-WE prothrombin, or E-WE preprothrombin expressed from the same coding DNA sequence.

The reason for the enhanced activity of a contemplated E. coli-derived recombinant E-WE thrombin enzyme compared to the same precursor being expressed in a mammalian cell is not known with certainty. However, that activity difference is believed to be due to imperfect cleavage of the mammalian-expressed precursor WE prethrombin-2, WE prothrombin or the like in which some of the up-stream residues from the thrombin A chain N-terminus remain bonded after the activation (cleavage) step. It is presumed that the replacement of the Trp and Glu residues with Ala residues in a contemplated E-WE thrombin causes some interference with post expression processing after E. coli expression that is not present in wild type thrombin or other mammalian-expressed thrombin mutants studied. This presumption is underscored by the fact that E-WE thrombin has a greatly reduced rate of proteolytic catalysis at the Arg284 auto-proteolytic site that reduces the length of the A chain by thirteen amino acid after the Factor Xa cleavage at Arg271. It is postulated that these additional residues on the mammalian-expressed WE construct, that are eliminated by introduction of the ecarin site at the 282-284 positions, reduce the anticoagulant potency of mammalian-expressed WE.

As can be seen from the data that follow in Table 3, several separate preparations of a contemplated E. coli-derived recombinant E-WE thrombin provided similar activity results that are within usual activity assay variances. The E-WE thrombin prepared using only ecarin exhibited similar activities that also were different from the activity of WE thrombin expressed in BHK cells.

A contemplated E-WE thrombin expressed in bacteria (e.g., E. coli) is free of glycosylation and can be used therapeutically, such as for enhancing hemostasis or treating and preventing thrombosis.

One advantage of the present invention is that it permits faster and more economical production of large quantities of anticoagulant (antithrombotic) thrombin. In particular, bacteria such as E. coli can be used to produce large batches of a E-WE thrombin enzyme for pharmaceutical development, therapy and other uses.

Compositions and Methods

A pharmaceutical composition or formulation is also contemplated that contains an effective amount of a contemplated bacteria-expressed E-WE thrombin enzyme dissolved or dispersed in a pharmaceutically acceptable carrier.

The pharmaceutical composition can be used for treating various diseases. For example, systemic and local use of the pharmaceutical composition of the present invention can be used for enhancing antithrombotic activity in a mammal at risk of or having intravascular blood coagulation. Another use for the pharmaceutical composition is to treat thrombotic diseases of one or more organs.

A contemplated E. coli-derived recombinant E-WE thrombin is dissolved or dispersed in a composition that is pharmaceutically acceptable and compatible with the active ingredient as is well known. The phrases "pharmaceutically acceptable" or "physiologically tolerable" refer to molecular entities and compositions that typically do not produce an allergic or similar untoward reaction, and the like, when administered to a host mammal.

The amount of E. coli-derived recombinant E-WE thrombin utilized in each administration is referred to as an anti-thrombotic effective amount and can vary widely, depending inter alia, upon the genus of the mammal to which a composition is administered, and the severity of the disease state being treated. An effective amount of an E. coli-derived recombinant E-WE thrombin enzyme at least temporarily improves the disease state for which the protein is administered.

A contemplated pharmaceutical composition for parenteral use comprises an effective amount of *E. coli*-derived antithrombotic E-WE thrombin dissolved or dispersed in a pharmaceutically acceptable carrier. A useful pharmaceutically acceptable carrier for parenteral administration is typically aqueous and is a liquid at room temperature.

An effective amount of a contemplated *E. coli*-derived antithrombotic E-WE thrombin administered per day is typically based on the weight of the recipient in kilograms. In one preferred embodiment, a dose of a pharmaceutical composition contains an antithrombotic effective amount of about 0.1 μg/kg/day to about 1 mg/kg/day of an *E. coli*-derived anticoagulant E-WE thrombin.

The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, are typically sterile injectable aqueous preparations, aqueous/alcoholic preparations, and can also include oleaginous suspensions that can be formulated according to the known art using suitable dispersing or wetting agents and suspending agents. A sterile injectable preparation can also be a sterile injectable solution or suspension in a nontoxic pharmaceutically acceptable diluent or solvent, for example, as a solution in ethanol, 1,3-butanediol or propylene glycol.

More specifically, among the pharmaceutically acceptable vehicles and solvents that can be employed are water, Ringer's solution, isotonic sodium chloride solution, and phosphate-buffered saline. Liquid parenteral compositions also include, for example, sterile water solutions of an active component or sterile solution of the active component in solvents comprising water, ethanol, or propylene glycol.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving or suspending the sterile compound in a previously sterilized solvent under sterile conditions. A contemplated composition can also be sterilized by passage through a beam of ionizing radiation. The use of conventional preservatives and antibacterial agents are also contemplated.

Suitable carriers for parenteral use can take a wide variety of forms depending on the intended use and are, for example, aqueous solutions containing saline, phosphate buffered saline (PBS), dextrose, glycerol, ethanol, or the like and combinations thereof. In addition, if desired, a composition can contain minor amounts of auxiliary pharmaceutically suitable substances such as wetting or emulsifying agents, preservatives, acids, bases, salts, sugars, pH buffering agents, which enhance the effectiveness of the composition.

Typical dosage for a contemplated anti-coagulant *E. coli*-expressed E-WE thrombin composition for systemic treatment of pathological coagulation (thrombosis) is about 0.1 μg/kg/hour to about 1 mg/kg/hour. A dose of a topical composition of *E. coli*-expressed procoagulant thrombin can contain about 10 μg to about 10 mg of enzyme.

A contemplated topical composition of *E. coli* expressed procoagulant thrombin analogs, including wt thrombin can use as its base a solution, spray, cream, a gel, medicated strips, or another acceptable base to deliver an effective amount of *E. coli*-derived procoagulant thrombin enzyme to the wound. Components of compositions for topical application (administration) are well known in the art and can be found in many texts such as Hoover, John E., *Remington's Pharmaceutical Sciences*, Mack Publishing Co., Easton, Pa.; 1975, or a later edition thereof.

Thus, for example, an external or topical preparation for application to a wound, incision or other break in the skin is contemplated. This composition contains an effective amount of an ecarin-activated procoagulant wild-type thrombin dissolved or dispersed in a gel base that also comprises about 0.5 to about 50% by weight of a water-soluble high molecular weight gellant (gelling agent). A contemplated gel base includes about 30 to about 70% by weight water, and zero to 70% by weight of a water-retaining agent. Further ingredients such as colorants, preservatives and other well known excipients can also be present. The procoagulant wild-type thrombin can also be used as a component of fibrin sealants, to be used topically, for bleeding control.

Illustrative gellants include naturally occurring gelling agents such as gelatin, starch, agar, mannan, alginic acid, gum arabic, gum tragacanth, karaya gum and locust bean gum, as well as synthetic gelling agents such as cross-linked polyacrylic acid, a salt of cross-linked polyacrylic acid, and copolymers thereof, dextrin, methylcellulose, methylcellulose sodium, carboxymethylcellulose, carboxymethylcellulose sodium, polyvinyl alcohol, partially hydrolyzed polyvinyl acetate, polyvinyl pyrrolidone, a copolymer of methyl vinyl ether and maleic anhydride. Illustrative water-retaining agents include ethylene glycol, diethylene glycol, polyethylene glycol, glycerin, sorbitol, martitol, propylene glycol and 1,3-butylene glycol.

A mammal in need of treatment and to which a pharmaceutical composition containing a contemplated *E. coli*-expressed anticoagulant E-WE thrombin is administered can be a primate including a human, an ape such as a chimpanzee or gorilla, a monkey such as a cynomolgus monkey or a macaque. The treated mammal also includes a laboratory animal such as a rat, mouse or rabbit, a companion animal such as a dog, cat, horse, or a food animal such as a cow or steer, sheep, lamb, pig, goat, llama or the like.

A contemplated composition can be administered to a mammal in need as is necessary to achieve the degree of anticoagulant activity desired. The E-WE thrombin molecule present in such a composition can be formed in situ (in vivo or in vitro) using activating enzymes and other well known cofactors present at the site of administration or within the body of the mammal. The E-WE thrombin can also be obtained prior to administration by admixture of i) a pharmaceutical composition containing a thrombin precursor such as E-WE preprothrombin, E-WE prothrombin or E-WE prethrobmin-2 and ii) the well known activating enzymes and cofactors as is illustrated hereinafter. More preferably, the E-WE thrombin is prepared from a E-WE thrombin precursor containing the amino acid residue sequence of SEQ ID NO:5 using ecarin to form the E-WE thrombin. Illustratively, a pharmaceutical composition containing a E-WE thrombin precursor fusion polypeptide can be contacted with ecarin-bound Sepharose® particles in an activation column that also contains antibody combining sites that bind to the cleaved N-terminal portion of the precursor prior to being administered to the mammal.

Methods for making the proteins and nucleotides used in the invention, as well as the methods of the invention taught in this disclosure utilize the conventional techniques of molecular genetics, cell biology, and biochemistry. Useful methods in molecular genetics, cell biology and biochemistry are described in *Molecular Cloning: A Laboratory Manual,* 2nd Ed. (Sambrook et al., 1989); *Oligonucleotide Synthesis* (M. J. Gait, ed., 1984); *Animal Cell Culture* (R. I. Freshney, ed., 1987); the series *Methods in Enzymology* (Academic Press, Inc.); "Gene Transfer Vectors for Mammalian Cells" (J. M. Miller & M. P. Calos, eds., 1987); *Current Protocols in Molecular Biology* and *Short Protocols in Molecular Biology, 3rd Edition* (F. M. Ausubel et al., eds., 1987 & 1995); and *Recombinant DNA Methodology II* (R. Wu ed., Academic Press 1995). Methods for peptide synthesis and manipulation are described in *Solid Phase Peptide Synthesis,* (J. M. Stewart & J. D. Young, 1984); *Solid Phase Peptide Synthesis: A Practical Approach* (E. Atherton & R. C. Sheppard, 1989); *The Chemical Synthesis of Peptides* (J. Jones, International Series of Monographs on Chemistry vol. 23, 1991); and *Solid Phase Peptide Synthesis,* (G. Barany & R. B. Merrifield, Chapter 1 of *The Peptides,* 1979); and *Bioconjugate Techniques* (G. T. Hermanson, 1996).

In some embodiments, a contemplated thrombin precursor is expressed in eukaryotic host cells. The thrombin precursor polypeptide so expressed is glycosylated. Illustrative eukaryotic cells include insect cells such as Sf9, and mammalian cell lines such as CHO, COS, 293, 293-EBNA, BHK, HeLa, NIH/3T3, and the like. Exemplary yeast host cells include *Saccharomyces cerevisiae, Pichia pastoris, Hansenula polymorpha, Kluyveromyces lactis, Schwanniomyces occidentis, Schizosaccharomyces pombe* and *Yarrowia lipolytica.*

More preferably, a contemplated thrombin precursor polypeptide is expressed in prokaryotic cells. Preferred prokaryotic cells are bacteria cells. Preferred bacteria cells are *E. coli* cells. Several strains of *Salmonella* such as *S. typhi* and *S. typhimurium* and *S. typhimurium-E. coli* hybrids can also be used to express a contemplated thrombin precursor. See, U.S. Pat. No. 6,024,961; U.S. Pat. No. 5,888,799; U.S. Pat. No. 5,387,744; U.S. Pat. No. 5,297,441; Ulrich et al., (1998) *Adv. Virus Res.,* 50:141-182; Tacket et al., (1997) *Infect. Immun.,* 65(8):3381-3385; Schödel et al., (1997) *Behring Inst. Mitt.,* 98:114-119; Nardelli-Haefliger et al., (1996) *Infect. Immun.,* 64(12):5219-5224; Londono et al., (1996) *Vaccine,* 14(6):545-552, and the citations therein.

A preferred *E. coli* strain useful herein for expression of a contemplated E-WE thrombin enzyme is BL21 (DE3). Additional *E. coli* strains useful for expression include XL-1, TB1, JM103, BLR, pUC8, pUC9, and pBR329 (Biorad Laboratories, Richmond, Calif.) and pPL and pKK223-3 available from (Pharmacia, Piscataway, N.J.).

A bacterial host that expresses a contemplated recombinant E-WE thrombin enzyme is prokaryote, such as *E. coli*, and a preferred vector includes a prokaryotic replicon; i.e., a DNA sequence having the ability to direct autonomous replication and maintenance of the recombinant DNA molecule extrachromosomally in a prokaryotic host cell transformed therewith. Such replicons are well known in the art. Vectors that include a prokaryotic replicon can also include a prokaryotic promoter region capable of directing the expression of a contemplated E-WE thrombin gene in a host cell, such as *E. coli*, transformed therewith.

Promoter sequences compatible with bacterial hosts are typically provided in plasmid vectors containing one or more convenient restriction sites for insertion of a contemplated DNA segment. Illustratively useful promoters and vectors include the Rec 7 promoter that is inducible by exogenously supplied nalidixic acid. A more preferred promoter is present in plasmid vector JHEX25 (Promega, Madison, Wis.) that is inducible by exogenously supplied isopropyl-β-D-thiogalacto-pyranoside (IPTG). Another preferred promoter, the tac (a hybrid of the trp and lac promoter/operator), is present in plasmid vector pKK223-3 (Pharmacia, Piscataway, N.J.) and is also inducible by exogenously supplied IPTG. Further promoters and promoter/operators include the araB, trp, lac, gal, T7, and the like are useful in accordance with the instant invention.

The exact details of the expression construct vary according to the particular host cell that is to be used as well as to the desired characteristics of the expression system, as is well known in the art. For example, for production in *S. cerevisiae*, the DNA encoding a thrombin precursor of the invention is placed into operable linkage with a promoter that is operable in *S. cerevisiae* and which has the desired characteristics (e.g., inducible/derepressible or constituative), such as GAL1-10, PHO5, PGK1, GDP1, PMA1, METS, CUP1, GAP, TPI, MF.alpha.1 and MF.alpha.2, as well as the hybrid promoters PGK/.alpha.2, TPI/.alpha.2, GAP/GAL, PGK/GAL, GAP/ADH2, GAP/PHO5, ADH2/PHO5, CYC1/GRE, and PGK/ARE and other promoters known in the art.

When other eukaryotic cells are the desired host cell, any promoter active in the host cell may be utilized. For example, when the desired host cell is a mammalian cell line, the promoter can be a viral promoter/enhancer (e.g., the herpes virus thymidine kinase (TK) promoter or a simian virus promoter (e.g., the SV40 early or late promoter) or the Adenovirus major late promoter, a long terminal repeat (LTR), such as the LTR from cytomegalovirus-(CMV), Rous sarcoma virus (RSV) or mouse mammary tumor virus (MMTV)) or a mammalian promoter, preferably an inducible promoter such as the metallothionein or glucocorticoid receptor promoters and the like.

Expression constructs can also include other DNA sequences appropriate for the intended host cell. For example, expression constructs for use in higher eukaryotic cell lines (e.g., vertebrate and insect cell lines) include a poly-adenylation site and can include an intron (including signals for processing the intron), as the presence of an intron appears to increase mRNA export from the nucleus in many systems. Additionally, a secretion signal sequence operable in the host cell is normally included as part of the construct. The secretion signal sequence can be the naturally occurring preprothrombin signal sequence, or it can be derived from another gene, such as human serum albumin, human prothrombin, human tissue plasminogen activator, or preproinsulin. Where the expression construct is intended for use in a prokaryotic cell, the expression construct can include a signal sequence that directs transport of the synthesized polypeptide into the periplasmic space or expression can be directed intracellularly.

Preferably, the expression construct also comprises a means for selecting for host cells that contain the expression construct (a "selectable marker"). Selectable markers are well known in the art. For example, the selectable marker can be a resistance gene, such as a antibiotic resistance gene (e.g., the neo.sup.r gene that confers resistance to the antibiotic gentamycin or the hyg.sup.r gene, that confers resistance to the antibiotic hygromycin). Alternatively, the selectable marker can be a gene that complements an auxotrophy of the host cell. If the host cell is a Chinese hamster ovary (CHO) cell that lacks the dihydrofolate reductase (dhfr) gene, for example CHO DUXB11 cells, a complementing dhfr gene would be preferred.

If the host cell is a yeast cell, the selectable marker is preferably a gene that complements an auxotrophy of the cell (for example, complementing genes useful in S. cerevisiae, P. pastoris and S. pombe include LEU2, TRP1, TRP1d, URA3, URA3d, HIS3, HIS4, ARG4, LEU2d), although antibiotic resistance markers such as SH BLE, which confers resistance to ZEOCIN®, can also be used. If the host cell is a prokaryotic or higher eukaryotic cell, the selectable marker is preferably an antibiotic resistance marker (e.g., neo.sup.r). Alternately, a separate selectable marker gene is not included in the expression vector, and the host cells are screened for the expression of a thrombin precursor (e.g., upon induction or derepression for controllable promoters, or after transfection for a constituitive promoter, fluorescence-activated cell sorting, FACS, may be used to select those cells which express the recombinant thrombin precursor). Preferably, the expression construct comprises a separate selectable marker gene.

A suitable promoter or enhancer, termination sequence and other functionalities for use in the expression of a thrombin precursor in given recombinant host cells are well known, as are suitable host cells for transfection with nucleic acid encoding the desired variant thrombin. It can be useful to use host cells that are capable of glycosylating the variant thrombin precursors, which typically include mammalian cells as discussed before.

In addition, host cells are suitable that have been used heretofore to express proteolytic enzymes or zymogens in recombinant cell culture, or which are known to already express high levels of such enzymes or zymogens in non-recombinant culture. In the latter case, if the endogenous enzyme or thrombin precursor is difficult to separate from a variant thrombin precursor, the endogenous gene should be removed by homologous recombination or its expression suppressed by cotransfecting the host cell with nucleic acid encoding an anti-sense sequence that is complementary to the RNA encoding the undesired polypeptide. In this case, the expression control sequences (e.g., promoter, enhancers, etc.) used by the endogenous expressed gene optimally are used to control expression of a thrombin precursor variant.

The following examples are for illustrative purposes and are in no way limiting.

Example 1

Protocol for E. coli Expression of Thrombin Mutant E-WE

The cDNA corresponding to prethrombin-2 sequence was cloned into pET21a vector (Novagen) using the EcoRI and the XhoI restriction sites. Site-directed mutagenesis was carried out using the Quikchange® site-directed mutagenesis kit from Strataqene (La Jolla, Calif.) to make the thrombin double mutation: W215A/E217A (WE), The E-WE prethrombin-2-encoding vector so prepared was transformed into BL21 (DE3) E. coli cells.

The E. coli cells were grown overnight (about 18 hours) in 10 mL of LB medium with 100 μg/mL ampicillin at 37° C. and 225 rpm. The next morning, 3 L of LB medium with 100 μg/mL of ampicillin was inoculated with the 10 mL overnight culture. Growth was continued at 37° C. and 225 rpm until the cells reached $OD_{600}$=0.6.

Prethrombin-2 expression was initiated by adding IPTG to a final concentration of 1 mM. The E. coli cells were cultured for an additional 4 hours. The cultures were spun at 3500 rpm for 20 minutes at 4° C.

The supernatant was discarded and the cell paste was frozen at −20° C. The cell paste, from 3 L of LB medium, was thawed at 37° C. and re-suspended in 50 mL of 50 mM Tris pH=7.4 at 25° C., 20 mM EDTA, 1% Triton® X-100, 20 mM DTT. Cells were sonicated on ice for 30 seconds×5 (about 1 minute rest) at constant duty, 5½ output, and time-hold. The well-homogenized cells were ultra-centrifuged for 30 minutes at 4° C., 30,000 rpm, using a Ti45 rotor.

The supernatant was discarded, and the pellet was re-suspended in 40 ml of 50 mM Tris pH=7.4 at 25° C., 20 mM EDTA, 1M NaCl using gentle vortexing and a spatula. The homogenate was centrifuged for 30 minutes, 30,000 rpm, 4° C. Supernatant was discarded, and the pellet was re-suspended in 40 ml of 50 mM Tris pH=7.4 at 25° C., 20 mM EDTA prior to centrifugation for 30 minutes, 30,000 rpm at 4° C. The supernatant was discarded, and the pellet was re-suspended in 27 mL of 7 M GdnHCl, 3 ml of 0.1% $H_2O$/TFA, and 30 mM L-cysteine, mixed and allowed to stand at 25° C. for 3 hours. The suspension was spun at 30,000 rpm at 4° C. for 45 minutes.

Refolding of prethrombin-2 was initiated by flash addition of the unfolded protein into 3 L of refolding buffer, 0.55 M L-arginine, 30% glycerol, 0.2 M NaCl, 1 mM L-cysteine, 0.1% polyoxyethylene 20 cetyl ether (Brij® 58), 50 mM Tris pH=8 at 25° C. The volume of refolding buffer used was such that the final GdnHCl concentration was not more than 0.15 M. During the addition of the unfolded protein, the refolding buffer was stirred at 250 rpm using a magnetic stirrer. After the addition of unfolded protein, the refolding buffer was left at room temperature for 12 hours without stirring.

The solution containing the refolded protein was concentrated from generally 3 L to 500 mL using a Flexstand®, from GE Healthcare (Piscataway, N.J.), with a 10 kDa mwc/1 m² hollow fiber cartridge. Using the Flexstand®, the refolded protein was diafiltered against 10 liters of 20 mM Tris pH=8 at 25° C., 50 mM NaCl. Precipitate was removed by centrifugation and filtration.

Protein solution was loaded onto a 5 mL heparin column, GE Healthcare, at 3 mL/minute. The bound protein was extensively washed by 100 mM NaCl, 10 mM Tris pH=8 at 25° C. before elution with a linear gradient of 100 mM to 1 M NaCl in 10 mM Tris, pH 8 at 25° C. The elution was monitored by UV spectroscopy. Prethrombin-2 was activated using a 200 nM final concentration of ecarin at 25° C.

To check for the completion of activation, SDS-PAGE was performed on the activated sample under reducing (by adding 5% v/v of β-mercaptoethanol) and non-reducing conditions.

The activated protein was diluted 4-fold and loaded on the heparin column. Bound protein was extensively washed with 100 mM NaCl, 10 mM Tris pH=8 at 25° C. before elution with a linear gradient of 100 mM to 1 M NaCl in 10 mM Tris, pH 8 at 25° C. Fractions with $OD_{280}$ greater than 0.1 were combined, concentrated and applied to detoxi-gel column to remove endotoxins. Concentration of the protein was determined by taking the $OD_{280}$. The extinction coefficient of recombinant E-WE thrombin at 280 nm is 1.83 $M^{-1}$ $cm^{-1}$.

The following is a description of the functional characterization of E-WE thrombin expressed in E. coli. E. coli does not have the capability to introduce glycosylation at the sole site in human thrombin at position N60g. The functional properties of WE thrombin mutant expressed from the BHK and from the E. coli expression systems are illustrated below in Table 1, with data for wild type (WT) thrombin as a control.

The BHK-expressed (mammalian-expressed) WT thrombin was prepared as discussed and reported in US Patent Publication 2010/0158890 and in Marino et al., (Jun. 18, 2010) *J. Biol. Chem.* 285(25):19145-19152. Relevant parameters for all physiological substrates are listed in Table 1 below. Solution conditions are 5 mM Tris pH=7.4 at 37° C., 0.1% PEG 8000, 145 mM NaCl.

TABLE 1

Catalytic activity (expressed as $k_{cat}/K_m$ in $mM^{-1}s^{-1}$) of WE thrombin mutant expressed in BHK or *E. coli*

|  | Fibrinogen | PAR 1 | Protein C |
|---|---|---|---|
| BHK* | 0.89 | 26 | 33 |
| *E. coli* | 0.16 | 10 | 22 |
| WT* | 17,000 | 26,000 | 220 |

*Cantwell and Di Cera, (2000) *J. Biol. Chem.*, 275(51): 39827-39830.

Example 2

In Vivo Studies with *E. coli*-Expressed Thrombin Mutant E-WE

BHK WE or *E. coli* E-WE were injected (250 µg/kg, slow bolus, 185 µL volume) into the femoral vein of C57B16 mice at 250 µg/kg. Blood was drawn by cardiac puncture into citrate at 10 minutes, plasma was prepared by centrifugation, and the plasma activated partial thromboplastin time (APTT) was determined (within 10 minutes of blood drawing).

The efficacy of the E-WE thrombin was also evaluated in conventional APTT assay using the PTT Automate® on Start® 4 instruments (Diagnostica Stago, Asnieres, France). For measurements of APTT (in seconds), fifty µL aliquots of platelet-poor plasma were transferred to disposable cuvettes (Diagnostica Stago, Parsippany, N.J.), and after addition of the APTT reagent and pre-incubation at 37° C., samples were run in duplicate. Therapeutic concentrations of DTIs (argatroban 0.5-1 µg/ml; lepirudin 0.1-1 µg/ml; bivalirudin 1-10 µg/ml), and heparin (0.2-0.5 U/ml) were used to pre-treat plasma. Effects of a E-WE thrombin mutant on APTT in DTI-treated plasma were evaluated after adding thrombin mutant (5 µg/ml, final concentration). Catalytic-site blocked thrombin (thrombin saturated with Phe-Pro-Arg-chlormethylketone; FPRck) was used at 100 µg/ml in some studies for comparison.

A plasma aliquot was incubated at a 37° C. for 60 minutes from blood drawing, and the APTT test was repeated. Decrease in APTT compared to the 10 minute sample indicates the presence of APC. Blood counts were determined to evaluate potential adverse effects (significant platelet consumption, bleeding).

The data are found in Table 2 below. The conclusion reached is that in mice, *E. coli* E-WE is a more potent anticoagulant than BHK-expressed WE.

TABLE 2

Evaluation of the anticoagulant activity of high dose BHK vs. *E. coli* E-WE in vivo, in mouse model of endogenous APC generation

|  | WT | 10 min* APTT | 60 min APTT | WBC* | RBC* | HCT* | PLT* |
|---|---|---|---|---|---|---|---|
| BHK WE | 24.3 | 38.7 | 25.4 | 12.52 | 9.77 | 42.8 | 870 |
|  | 22 | 35.4 | 14.9 | 10.16 | 9.1 | 40.9 | 1053 |
|  | 23.2 | 35.7 | 18.4 | 9.52 | 9.54 | 43.3 | 1040 |
| *E. coli* | 21 | 47.8 | 24.4 | 9.4 | 9.49 | 42.4 | 873 |
| E-WE | 20.5 | 90.9 | 33.9 | 3.8 | 8.39 | 36.7 | 795 |
|  | 22.3 | 73.9 | 29.9 | 9.64 | 9.04 | 40.2 | 976 |
|  | 24 | 55.9 | 28.4 | 9.94 | 9.04 | 40.1 | 927 |
|  | 20.2 | 55.9 | 29.9 | 12.28 | 9.75 | 42.9 | 996 |
|  | 21.4 | 76.1 | 29.9 | 12.9 | 9.18 | 40.7 | 857 |
| Control | 25 | 24.4 | 22.8 | 7.78 | 8.97 | 40.5 | 1007 |

*min = minute; red blood cell count (RBC); white blood cell count (WBC); hematocrit (HCT); and platelet count (PLT)

Example 3

Comparison of WE Properties on Expression in BHK or *E. coli*

Table 3, below, presents a summary of the functional properties of WE thrombin prepared from WE prethrombin-2 expressed in BHK and *E. coli* cells. Values are listed for the $k_{cat}/K_m$ for the hydrolysis of a chromogenic substrate (FPR), and the physiological substrates fibrinogen (FpA), PAR 1 and protein C (PC) activation.

In the case of wild-type thrombin, BHK and *E. coli* productions are equivalent. In the case of a WE thrombin, BHK produces a construct with significantly higher activity toward FPR and fibrinogen. A E-WE thrombin made in *E. coli* consistently shows lower specificity toward fibrinogen compared to the BHK-expressed construct resulting in higher anticoagulant activity. This same effect is also seen in vivo.

Included in the Table 3 are data from BHK and *E. coli* production of another anticoagulant thrombin mutant, Δ146-149e. As shown in Table 3, below, there is no difference in anticoagulant activity between Δ146-149e constructs expressed in either BHK and *E. coli*.

An unexpected result happens for a WE thrombin prepared from a thrombin precursor expressed in *E. coli*, most likely due to retention of a longer A chain and part of Fragment 2 (incompletely cleaved) in the BHK construct due to the different activation. There is an Arg-Thr cleavage site sequence about 13 residues upstream of the usual Arg-Thr cleavage site within the Fragment 2 position of the molecule. That unexpected result is a markedly lower activity of the E-WE thrombin prepared from bacteria-expressed prethrombin-2 and that expressed in BHK cells.

The table below also contains similar data for E-WE thrombin expressed in *E. coli* and prepared by activation using only ecarin, whose preparation is discussed hereinafter.

TABLE 3

Summary of the functional properties of thrombin constructs made in BHK and *E. coli*

|  | Protein C $(mM^{-1}s^{-1})$ | Fibrinogen $(\mu M^{-1}s^{-1})$ | Par 1 $(\mu M^{-1}s^{-1})$ | FPR $(\mu M^{-1}s^{-1})$ | Activation Method |
|---|---|---|---|---|---|
| *E. coli* WT | 220 ± 1 | 9.6 ± 0.5 | 24 ± 1 | 26 ± 1 | Ecarin |
| BHK WT | 220 ± 1 | 17 ± 1 | 26 ± 1 | 37 ± 2 | Prothrombinase |
| *E. coli* Δ146-149e | 35 ± 1 | 0.11 ± 0.01 | 0.13 ± 0.01 | 1.6 ± 0.1 | Prothrombinase, Ecarin |
| BHK Δ146-149e | 13 ± 1 | 0.071 ± 0.004 | 0.12 ± 0.01 | 0.26 ± 0.01 | Ecarin |

TABLE 3-continued

Summary of the functional properties of thrombin constructs made in BHK and E. coli

| | Protein C ($mM^{-1}s^{-1}$) | Fibrinogen ($\mu M^{-1}s^{-1}$) | Par 1 ($\mu M^{-1}s^{-1}$) | FPR ($\mu M^{-1}s^{-1}$) | Activation Method |
|---|---|---|---|---|---|
| E. coli E-WE (Lot 1) FZ | 9.26 ± 0.036 | 0.000161 ± 1.9e−8 | 0.010 ± 1.3e−5 | 0.0011 ± 1.08e−6 | Prothrombinase + Ecarin |
| E. coli E-WE (Lot 2) | 25 ± 1 | 0.00013 ± 0.00001 | 0.0040 ± 0.0002 | 0.0015 ± 0.0001 | Prothrombinase Ecarin, AC |
| E. coli E-WE (Lot 3) | 14 ± 1 | 0.0011 ± 0.0001 | 0.096 ± 0.005 | 0.0023 ± 0.0001 | Ecarin, AC |
| E. coli E-WE (Lot 4) | 16 ± 1 | 0.00019 ± 0.00001 | 0.032 ± 0.002 | 0.0012 ± 0.0001 | Prothrombinase, Ecarin, AC |
| E. coli E-WE (Lot 5) | 3.7 ± 0.07 | 0.00017 ± 7e−5 | 0.0094 ± 3.9e−4 | 0.0016 ± 2.03e−6 | Prothrombinase + Ecarin |
| E. coli E-WE (Lot 6, FZ) | 24.6 ± 0.045 | 0.000184 ± 4.12e−9 | 0.0085 ± 3.9e−4 | 0.0035 ± 2.9e−5 | Prothrombinase + Ecarin |
| E. coli E-WE Two ecarin sites Lot 1 | 26.6 ± 0.062 | 0.00027 ± 1.1e−4 | 0.0099 ± 1.27e−4 | 0.0014 ± 6e−6 | Ecarin Only |
| BHK WE, * 100 nM TM | 33 ± 2 | 0.00089 ± 7e−5 | 0.026 ± 1e−3 | 0.0028 ± 1e−5 | Prothrombinase Only |
| BHK WE | 4.1 ± 0.3 | 0.0052 ± 0.0003 | 0.017 ± 0.001 | 0.018 ± 0.002 | Prothrombinase, Ecarin |

* Cantwell and Di Cera, (2000) *J. Biol. Chem.*, 275(51): 39827-39830.

The above data were collected under the following protein C reaction conditions: 50 nM thrombomodulin (TM), 50 nM protein C (PC), 0.5 nM thrombin and the following buffer conditions: 145 mM NaCl, 5 mM Tris pH 7.4 at 37° C., 0.1% PEG 8000.

The table above summarizes the results of different lots of E-WE thrombin prepared from prethrombin-2 expressed in *E. coli* cells and WE thrombin prepared from prethrombin-1 expressed in BHK cells, activated with prothrombinase and *Echis carinatus* snake venom prothrombin activator (ecarin) as the *E. coli* construct. There is high reproducibility in the different lots activated this way, but a large difference in fibrinogen cleavage caused by WE thrombin prepared from prethrombin-1 expressed in BHK cells and E-WE thrombin produced from prethrombin-2 expressed in *E. coli*.

There is also a large difference between E-WE thrombin prepared from prethrombin-2 expressed in *E. coli* and activated with prothrombinase plus ecarin vs the use of ecarin and AC venoms.

The specifics of why expression of WE prethrombin-1 in BHK and E-WE prethrombin-2 in *E. coli* produce different activities of WE thrombin even after the same activation process remain unknown. However, the results are reproducible and the data from in vivo studies confirm the data obtained from in vitro studies.

It is noted that wild type thrombin and the anticoagulant mutant Δ146-149e feature the same properties when made from corresponding prethrombin molecules expressed in BHK or *E. coli* cells by the same coding sequence. There is therefore something special about E-WE thrombin prepared from *E. coli*-expressed prethrombin-2 that is activated with prothrombinase and ecarin that produces an enhanced anticoagulant profile.

Example 4

E-WE Thrombin Prepared from an Ecarin Cleavage Site at Residues 325-327

The wild-type prethrombin-2 sequence contains residues FNPRTF (SEQ ID NO:11) at positions 324-329 from the N-terminus of the preprothrombin polypeptide. That sequence was replaced with the engineered sequence FDGRTF (SEQ ID NO:12), that placed the ecarin cleavage site—DGR—at positions 325-327 of the expressed sequence. Only two amino acid residues needed to be changed. The naturally-occurring cleavage site for ecarin is YIDGRIV (SEQ ID NO:13), whose cleavage separates the thrombin A and B chains.

To accomplish these changes, two primers were designed coding for the altered sequence in both the 5' to 3' and reverse complement direction. Using PCR site directed mutagenesis, the mutation was made and ultimately confirmed with DNA sequencing. The new plasmid construct for a E-WE thrombin precursor with an additional ecarin site was used to over express the protein in an established *E. coli* expression system.

Upon refolding and initial purification as discussed above, the E-WE prethrombin-2 was processed using the snake venom derived protease ecarin. The expected cleavage took place between the A and B chains to form an A chain-extended E-WE thrombin. Cleavage also occurred at the engineered ecarin site that had been introduced preceding the A chain. This cleavage resulted in a properly processed N-terminus as confirmed by N-terminal sequencing of both the A and B chains.

When subjected to standard in vitro biochemical characterization, the E-WE-thrombin produced using this new processing method behaved in an equivalent manner to E-WE-thrombin produced using the original vector (Table 3, above) and activated by prothrombinase complex and ecarin.

The alternative pathway promoted by FXa proceeds through the generation of the inactive precursor prethrombin-2 by cleaving at Arg271 and then activation to thrombin by cleaving at Arg320. Another strategy to produce thrombin from the inactive precursor prothrombin has been developed by using ecarin, a zinc metalloprotease mostly present in different snake venoms. Indeed, ecarin has a FXa-similar activity, specifically cleaves the C-terminal of Arg320 and irreversibly activates prothrombin/prethrombin-2 into meizothrombin/thrombin.

Once activated, meizothrombin/thrombin itself cleaves at Arg284 to generate the correct A chain, and thus, the mature enzyme. As occurs in the absence of prothrombinase complex or in the case of a poorly active thrombin mutant, a single ecarin cleavage is not sufficient to generate the mature and physiologically relevant thrombin enzyme.

LISTED SEQUENCES

WE Thrombin
SEQ ID NO: 1
TFGSGEADCG LRPLFEKKSL EDKTERELLE SYIDGRIVEG

SDAEIGMSPW QVMLFRKSPQ ELLCGASLIS DRWVLTAAHC

LLYPPWDKNF TENDLLVRIG KHSRTRYERN IEKISMLEKI

YIHPRYNWRE NLDRDIALMK LKKPVAFSDY IHPVCLPDRE

TAASLLQAGY KGRVTGWGNL KETWTANVGK GQPSVLQVVN

LPIVERPVCK DSTRIRITDN MFCAGYKPDE GKRGDACEGD

SGGPFVMKSP FNNRWYQMGI VSAGAGCDRD GKYGFYTHVF

RLKKWIQKVI DQFGE

Thrombin
SEQ ID NO: 2
TFGSGEADCG LRPLFEKKSL EDKTERELLE SYIDGRIVEG

SDAEIGMSPW QVMLFRKSPQ ELLCGASLIS DRWVLTAAHC

LLYPPWDKNF TENDLLVRIG KHSRTRYERN IEKISMLEKI

YIHPRYNWRE NLDRDIALMK LKKPVAFSDY IHPVCLPDRE

TAASLLQAGY KGRVTGWGNL KETWTANVGK GQPSVLQVVN

LPIVERPVCK DSTRIRITDN MFCAGYKPDE GKRGDACEGD

SGGPFVMKSP FNNRWYQMGI VSWGEGCDRD GKYGFYTHVF

RLKKWIQKVI DQFGE

Preprothrombin
SEQ ID NO: 3
MAHVRGLQLP GCLALAALCS LVHSQHVFLA PQQARSLLQR

VRRANTFLEE VRKGNLEREC VEETCSYEEA FEALESSTAT

DVFWAKYTAC ETARTPRDKL AACLEGNCAE GLGTNYRGHV

NITRSGIECQ LWRSRYPHKP EINSTTHPGA DLQENFCRNP

DSSTTGPWCY TTDPTVRRQE CSIPVCGQDQ VTVAMTPRSE

GSSVNLSPPL EQCVPDRGQQ YQGRLAVTTH GLPCLAWASA

QAKALSKHQD FNSAVQLVEN FCRNPDGDEE GVWCYVAGKP

GDFGYCDLNY CEEAVEEETG DGLDEDSDRA IEGRTATSEY

QTFFNPRTFG SGEADCGLRP LFEKKSLEDK TERELLESYI

DGRIVEGSDA EIGMSPWQVM LFRKSPQELL CGASLISDRW

VLTAAHCLLY PPWDKNFTEN DLLVRIGKHS RTRYERNIEK

ISMLEKIYIH PRYNWRENLD RDIALMKLKK PVAFSDYIHP

VCLPDRETAA SLLQAGYKGR VTGWGNLKET WTANVGKGQP

SVLQVVNLPI VERPVCKDST RIRITDNMFC AGYKPDEGKR

GDACEGDSGG PFVMKSPFNN RWYQMGIVSW GEGCDRDGKY

GFYTHVFRLK KWIQKVIDQF GE

Ecarin-activatable E-WE Preprothrombin
SEQ ID NO: 4
MAHVRGLQLP GCLALAALCS LVHSQHVFLA PQQARSLLQR

VRRANTFLEE VRKGNLEREC VEETCSYEEA FEALESSTAT

DVFWAKYTAC ETARTPRDKL AACLEGNCAE GLGTNYRGHV

NITRSGIECQ LWRSRYPHKP EINSTTHPGA DLQENFCRNP

DSSTTGPWCY TTDPTVRRQE CSIPVCGQDQ VTVAMTPRSE

GSSVNLSPPL EQCVPDRGQQ YQGRLAVTTH GLPCLAWASA

QAKALSKHQD FNSAVQLVEN FCRNPDGDEE GVWCYVAGKP

GDFGYCDLNY CEEAVEEETG DGLDEDSDRA IEGRTATSEY

QTFFDGRTFG SGEADCGLRP LFEKKSLEDK TERELLESYI

DGRIVEGSDA EIGMSPWQVM LFRKSPQELL CGASLISDRW

VLTAAHCLLY PPWDKNFTEN DLLVRIGKHS RTRYERNIEK

ISMLEKIYIH PRYNWRENLD RDIALMKLKK PVAFSDYIHP

VCLPDRETAA SLLQAGYKGR VTGWGNLKET WTANVGKGQP

SVLQVVNLPI VERPVCKDST RIRITDNMFC AGYKPDEGKR

GDACEGDSGG PFVMKSPFNN RWYQMGIVSA GAGCDRDGKY

GFYTHVFRLK KWIQKVIDQF GE

Ecarin-activatable E-WE Prethrombin-2
SEQ ID NO: 5
TATSEYQTFF DGRTFGSGEA DCGLRPLFEK KSLEDKTERE

LLESYIDGRI VEGSDAEIGM SPWQVMLFRK SPQELLCGAS

LISDRWVLTA AHCLLYPPWD KNFTENDLLV RIGKHSRTRY

ERNIEKISML EKIYIHPRYN WRENLDRDIA LMKLKKPVAF

SDYIHPVCLP DRETAASLLQ AGYKGRVTGW GNLKETWTAN

VGKGQPSVLQ VVNLPIVERP VCKDSTRIRI TDNMFCAGYK

PDEGKRGDAC EGDSGGPFVM KSPFNNRWYQ MGIVSAGAGC

DRDGKYGFYT HVFRLKKWIQ KVIDQFGE

Ecarin-activatable Preprothrombin
SEQ ID NO: 6
MAHVRGLQLP GCLALAALCS LVHSQHVFLA PQQARSLLQR

VRRANTFLEE VRKGNLEREC VEETCSYEEA FEALESSTAT

DVFWAKYTAC ETARTPRDKL AACLEGNCAE GLGTNYRGHV

NITRSGIECQ LWRSRYPHKP EINSTTHPGA DLQENFCRNP

DSSTTGPWCY TTDPTVRRQE CSIPVCGQDQ VTVAMTPRSE

GSSVNLSPPL EQCVPDRGQQ YQGRLAVTTH GLPCLAWASA

QAKALSKHQD FNSAVQLVEN FCRNPDGDEE GVWCYVAGKP

GDFGYCDLNY CEEAVEEETG DGLDEDSDRA IEGRTATSEY

QTFFDGRTFG SGEADCGLRP LFEKKSLEDK TERELLESYI

DGRIVEGSDA EIGMSPWQVM LFRKSPQELL CGASLISDRW

VLTAAHCLLY PPWDKNFTEN DLLVRIGKHS RTRYERNIEK

ISMLEKIYIH PRYNWRENLD RDIALMKLKK PVAFSDYIHP

VCLPDRETAA SLLQAGYKGR VTGWGNLKET WTANVGKGQP

SVLQVVNLPI VERPVCKDST RIRITDNMFC AGYKPDEGKR

```
GDACEGDSGG PFVMKSPFNN RWYQMGIVSW GEGCDRDGKY
GFYTHVFRLK KWIQKVIDQF GE
Ecarin-activatable Prethrombin-2
                                 SEQ ID NO: 7
TATSEYQTFF DGRTFGSGEA DCGLRPLFEK KSLEDKTERE
LLESYIDGRI VEGSDAEIGM SPWQVMLFRK SPQELLCGAS
LISDRWVLTA AHCLLYPPWD KNFTENDLLV RIGKHSRTRY
ERNIEKISML EKIYIHPRYN WRENLDRDIA LMKLKKPVAF
SDYIHPVCLP DRETAASLLQ AGYKGRVTGW GNLKETWTAN
VGKGQPSVLQ VVNLPIVERP VCKDSTRIRI TDNMFCAGYK
PDEGKRGDAC EGDSGGPFVM KSPFNNRWYQ MGIVSWGEGC
DRDGKYGFYT HVFRLKKWIQ KVIDQFGE
Ecarin-activatable Δ146-149e Prethrombin-2
                                 SEQ ID NO: 8
TATSEYQTFF DGRTFGSGEA DCGLRPLFEK KSLEDKTERE
LLESYIDGRI VEGSDAEIGM SPWQVMLFRK SPQELLCGAS
LISDRWVLTA AHCLLYPPWD KNFTENDLLV RIGKHSRTRY
ERNIEKISML EKIYIHPRYN WRENLDRDIA LMKLKKPVAF
SDYIHPVCLP DRETAASLLQ AGYKGRVTGW GNLKGKGQPS
VLQVVNLPIV ERPVCKDSTR IRITDNMFCA GYKPDEGKRG
DACEGDSGGP FVMKSPFNNR WYQMGIVSWG EGCDRDGKYG
FYTHVFRLKK WIQKVIDQFG E
WE Preprothrombin
                                 SEQ ID NO: 9
MAHVRGLQLP GCLALAALCS LVHSQHVFLA PQQARSLLQR
VRRANTFLEE VRKGNLEREC VEETCSYEEA FEALESSTAT
DVFWAKYTAC ETARTPRDKL AACLEGNCAE GLGTNYRGHV
NITRSGIECQ LWRSRYPHKP EINSTTHPGA DLQENFCRNP
DSSTTGPWCY TTDPTVRRQE CSIPVCGQDQ VTVAMTPRSE
GSSVNLSPPL EQCVPDRGQQ YQGRLAVTTH GLPCLAWASA
QAKALSKHQD FNSAVQLVEN FCRNPDGDEE GVWCYVAGKP
GDFGYCDLNY CEEAVEEETG DGLDEDSDRA IEGRTATSEY
QTFFNPRTFG SGEADCGLRP LFEKKSLEDK TERELLESYI
DGRIVEGSDA EIGMSPWQVM LFRKSPQELL CGASLISDRW
VLTAAHCLLY PPWDKNFTEN DLLVRIGKHS RTRYERNIEK
ISMLEKIYIH PRYNWRENLD RDIALMKLKK PVAFSDYIHP
VCLPDRETAA SLLQAGYKGR VTGWGNLKET WTANVGKGQP
SVLQVVNLPI VERPVCKDST RIRITDNMFC AGYKPDEGKR
GDACEGDSGG PFVMKSPFNN RWYQMGIVSA GAGCDRDGKY
GFYTHVFRLK KWIQKVIDQF GE
WE Prethrombin-2
                                 SEQ ID NO: 10
TATSEYQTFF NPRTFGSGEA DCGLRPLFEK KSLEDKTERE
LLESYIDGRI VEGSDAEIGM SPWQVMLFRK SPQELLCGAS
LISDRWVLTA AHCLLYPPWD KNFTENDLLV RIGKHSRTRY
ERNIEKISML EKIYIHPRYN WRENLDRDIA LMKLKKPVAF
SDYIHPVCLP DRETAASLLQ AGYKGRVTGW GNLKETWTAN
VGKGQPSVLQ VVNLPIVERP VCKDSTRIRI TDNMFCAGYK
PDEGKRGDAC EGDSGGPFVM KSPFNNRWYQ MGIVSAGAGC
DRDGKYGFYT HVFRLKKWIQ KVIDQFGE
                                 SEQ ID NO: 11
FNPRTF
                                 SEQ ID NO: 12
FDGRTF
                                 SEQ ID NO: 13
YIDGRIV
Ecarin-activatable E-WE Thrombin Precursor A
                                 SEQ ID NO: 14
DGRTFGSGEA DCGLRPLFEK KSLEDKTERE LLESYIDGRI
VEGSDAEIGM SPWQVMLFRK SPQELLCGAS LISDRWVLTA
AHCLLYPPWD KNFTENDLLV RIGKHSRTRY ERNIEKISML
EKIYIHPRYN WRENLDRDIA LMKLKKPVAF SDYIHPVCLP
DRETAASLLQ AGYKGRVTGW GNLKETWTAN VGKGQPSVLQ
VVNLPIVERP VCKDSTRIRI TDNMFCAGYK PDEGKRGDAC
EGDSGGPFVM KSPFNNRWYQ MGIVSAGAGC DRDGKYGFYT
HVFRLKKWIQ KVIDQFGE
                                 SEQ ID NO: 15
EGRTFGSGEA DCGLRPLFEK KSLEDKTERE LLESYIDGRI
VEGSDAEIGM SPWQVMLFRK SPQELLCGAS LISDRWVLTA
AHCLLYPPWD KNFTENDLLV RIGKHSRTRY ERNIEKISML
EKIYIHPRYN WRENLDRDIA LMKLKKPVAF SDYIHPVCLP
DRETAASLLQ AGYKGRVTGW GNLKETWTAN VGKGQPSVLQ
VVNLPIVERP VCKDSTRIRI TDNMFCAGYK PDEGKRGDAC
EGDSGGPFVM KSPFNNRWYQ MGIVSAGAGC DRDGKYGFYT
HVFRLKKWIQ KVIDQFGE
Ecarin-activatable Thrombin Precursor A
                                 SEQ ID NO: 16
DGRTFGSGEA DCGLRPLFEK KSLEDKTERE LLESYIDGRI
VEGSDAEIGM SPWQVMLFRK SPQELLCGAS LISDRWVLTA
AHCLLYPPWD KNFTENDLLV RIGKHSRTRY ERNIEKISML
EKIYIHPRYN WRENLDRDIA LMKLKKPVAF SDYIHPVCLP
DRETAASLLQ AGYKGRVTGW GNLKETWTAN VGKGQPSVLQ
VVNLPIVERP VCKDSTRIRI TDNMFCAGYK PDEGKRGDAC
EGDSGGPFVM KSPFNNRWYQ MGIVSWGEGC DRDGKYGFYT
HVFRLKKWIQ KVIDQFGE
                                 SEQ ID NO: 17
EGRTFGSGEA DCGLRPLFEK KSLEDKTERE LLESYIDGRI
VEGSDAEIGM SPWQVMLFRK SPQELLCGAS LISDRWVLTA
AHCLLYPPWD KNFTENDLLV RIGKHSRTRY ERNIEKISML
```

EKIYIHPRYN WRENLDRDIA LMKLKKPVAF SDYIHPVCLP

DRETAASLLQ AGYKGRVTGW GNLKETWTAN VGKGQPSVLQ

VVNLPIVERP VCKDSTRIRI TDNMFCAGYK PDEGKRGDAC

EGDSGGPFVM KSPFNNRWYQ MGIVSWGEGC DRDGKYGFYT

HVFRLKKWIQ KVIDQFGE

Wild Type Prothrombin
SEQ ID NO: 18

ANTFLEEVRK GNLERECVEE TCSYEEAFEA LESSTATDVF

WAKYTACETA RTPRDKLAAC LEGNCAEGLG TNYRGHVNIT

RSGIECQLWR SRYPHKPEIN STTHPGADLQ ENFCRNPDSS

TTGPWCYTTD PTVRRQECSI PVCGQDQVTV AMTPRSEGSS

VNLSPPLEQC VPDRGQQYQG RLAVTTHGLP CLAWASAQAK

ALSKHQDFNS AVQLVENFCR NPDGDEEGVW CYVAGKPGDF

GYCDLNYCEE AVEEETGDGL DEDSDRAIEG RTATSEYQTF

FNPRTFGSGE ADCGLRPLFE KKSLEDKTER ELLESYIDGR

IVEGSDAEIG MSPWQVMLFR KSPQELLCGA SLISDRWVLT

AAHCLLYPPW DKNFTENDLL VRIGKHSRTR YERNIEKISM

LEKIYIHPRY NWRENLDRDI ALMKLKKPVA FSDYIHPVCL

PDRETAASLL QAGYKGRVTG WGNLKETWTA NVGKGQPSVL

QVVNLPIVER PVCKDSTRIR ITDNMFCAGY KPDEGKRGDA

CEGDSGGPFV MKSPFNNRWY QMGIVSWGEG CDRDGKYGFY

THVFRLKKWI QKVIDQFGE

WE Prothrombin
SEQ ID NO: 19

ANTFLEEVRK GNLERECVEE TCSYEEAFEA LESSTATDVF

WAKYTACETA RTPRDKLAAC LEGNCAEGLG TNYRGHVNIT

RSGIECQLWR SRYPHKPEIN STTHPGADLQ ENFCRNPDSS

TTGPWCYTTD PTVRRQECSI PVCGQDQVTV AMTPRSEGSS

VNLSPPLEQC VPDRGQQYQG RLAVTTHGLP CLAWASAQAK

ALSKHQDFNS AVQLVENFCR NPDGDEEGVW CYVAGKPGDF

GYCDLNYCEE AVEEETGDGL DEDSDRAIEG RTATSEYQTF

FNPRTFGSGE ADCGLRPLFE KKSLEDKTER ELLESYIDGR

IVEGSDAEIG MSPWQVMLFR KSPQELLCGA SLISDRWVLT

AAHCLLYPPW DKNFTENDLL VRIGKHSRTR YERNIEKISM

LEKIYIHPRY NWRENLDRDI ALMKLKKPVA FSDYIHPVCL

PDRETAASLL QAGYKGRVTG WGNLKETWTA NVGKGQPSVL

QVVNLPIVER PVCKDSTRIR ITDNMFCAGY KPDEGKRGDA

CEGDSGGPFV MKSPFNNRWY QMGIVSAGAG CDRDGKYGFY

THVFRLKKWI QKVIDQFGE

Ecarin-activatable E-WE Prothrombin
SEQ ID NO: 20

ANTFLEEVRK GNLERECVEE TCSYEEAFEA LESSTATDVF

WAKYTACETA RTPRDKLAAC LEGNCAEGLG TNYRGHVNIT

RSGIECQLWR SRYPHKPEIN STTHPGADLQ ENFCRNPDSS

TTGPWCYTTD PTVRRQECSI PVCGQDQVTV AMTPRSEGSS

VNLSPPLEQC VPDRGQQYQG RLAVTTHGLP CLAWASAQAK

ALSKHQDFNS AVQLVENFCR NPDGDEEGVW CYVAGKPGDF

GYCDLNYCEE AVEEETGDGL DEDSDRAIEG RTATSEYQTF

FDGRTFGSGE ADCGLRPLFE KKSLEDKTER ELLESYIDGR

IVEGSDAEIG MSPWQVMLFR KSPQELLCGA SLISDRWVLT

AAHCLLYPPW DKNFTENDLL VRIGKHSRTR YERNIEKISM

LEKIYIHPRY NWRENLDRDI ALMKLKKPVA FSDYIHPVCL

PDRETAASLL QAGYKGRVTG WGNLKETWTA NVGKGQPSVL

QVVNLPIVER PVCKDSTRIR ITDNMFCAGY KPDEGKRGDA

CEGDSGGPFV MKSPFNNRWY QMGIVSAGAG CDRDGKYGFY

THVFRLKKWI QKVIDQFGE

SEQ ID NO: 21

ANTFLEEVRK GNLERECVEE TCSYEEAFEA LESSTATDVF

WAKYTACETA RTPRDKLAAC LEGNCAEGLG TNYRGHVNIT

RSGIECQLWR SRYPHKPEIN STTHPGADLQ ENFCRNPDSS

TTGPWCYTTD PTVRRQECSI PVCGQDQVTV AMTPRSEGSS

VNLSPPLEQC VPDRGQQYQG RLAVTTHGLP CLAWASAQAK

ALSKHQDFNS AVQLVENFCR NPDGDEEGVW CYVAGKPGDF

GYCDLNYCEE AVEEETGDGL DEDSDRAIEG RTATSEYQTF

FEGRTFGSGE ADCGLRPLFE KKSLEDKTER ELLESYIDGR

IVEGSDAEIG MSPWQVMLFR KSPQELLCGA SLISDRWVLT

AAHCLLYPPW DKNFTENDLL VRIGKHSRTR YERNIEKISM

LEKIYIHPRY NWRENLDRDI ALMKLKKPVA FSDYIHPVCL

PDRETAASLL QAGYKGRVTG WGNLKETWTA NVGKGQPSVL

QVVNLPIVER PVCKDSTRIR ITDNMFCAGY KPDEGKRGDA

CEGDSGGPFV MKSPFNNRWY QMGIVSAGAG CDRDGKYGFY

THVFRLKKWI QKVIDQFGE

E-WE Thrombin with Ecarin Site
SEQ ID NO: 22

DGRTFGSGE ADCGLRPLFE KKSLEDKTER ELLESYIDGR

IVEGSDAEIG MSPWQVMLFR KSPQELLCGA SLISDRWVLT

AAHCLLYPPW DKNFTENDLL VRIGKHSRTR YERNIEKISM

LEKIYIHPRY NWRENLDRDI ALMKLKKPVA FSDYIHPVCL

PDRETAASLL QAGYKGRVTG WGNLKETWTA NVGKGQPSVL

QVVNLPIVER PVCKDSTRIR ITDNMFCAGY KPDEGKRGDA

CEGDSGGPFV MKSPFNNRWY QMGIVSAGAG CDRDGKYGFY

THVFRLKKWI QKVIDQFGE

SEQ ID NO: 23

EGRTFGSGE ADCGLRPLFE KKSLEDKTER ELLESYIDGR

IVEGSDAEIG MSPWQVMLFR KSPQELLCGA SLISDRWVLT

AAHCLLYPPW DKNFTENDLL VRIGKHSRTR YERNIEKISM

```
LEKIYIHPRY NWRENLDRDI ALMKLKKPVA FSDYIHPVCL

PDRETAASLL QAGYKGRVTG WGNLKETWTA NVGKGQPSVL

QVVNLPIVER PVCKDSTRIR ITDNMFCAGY KPDEGKRGDA

CEGDSGGPFV MKSPFNNRWY QMGIVSAGAG CDRDGKYGFY

THVFRLKKWI QKVIDQFGE

Wild Type Thrombin with Ecarin Site
                                    SEQ ID NO: 24
  DGRTFG Leu Leu Tyr Pro Pro Trp Asp Lys Asn Phe Thr Glu Asn Asp Leu Leu
                85                  90                  95

Val Arg Ile Gly Lys His Ser Arg Thr Arg Tyr Glu Arg Asn Ile Glu
            100                 105                 110

Lys Ile Ser Met Leu Glu Lys Ile Tyr Ile His Pro Arg Tyr Asn Trp
        115                 120                 125

Arg Glu Asn Leu Asp Arg Asp Ile Ala Leu Met Lys Leu Lys Lys Pro
    130                 135                 140

Val Ala Phe Ser Asp Tyr Ile His Pro Val Cys Leu Pro Asp Arg Glu
145                 150                 155                 160

Thr Ala Ala Ser Leu Leu Gln Ala Gly Tyr Lys Gly Arg Val Thr Gly
                165                 170                 175

Trp Gly Asn Leu Lys Glu Thr Trp Thr Ala Asn Val Gly Lys Gly Gln
            180                 185                 190

Pro Ser Val Leu Gln Val Val Asn Leu Pro Ile Val Glu Arg Pro Val
        195                 200                 205

Cys Lys Asp Ser Thr Arg Ile Arg Ile Thr Asp Asn Met Phe Cys Ala
    210                 215                 220

Gly Tyr Lys Pro Asp Glu Gly Lys Arg Gly Asp Ala Cys Glu Gly Asp
225                 230                 235                 240

Ser Gly Gly Pro Phe Val Met Lys Ser Pro Phe Asn Asn Arg Trp Tyr
                245                 250                 255

Gln Met Gly Ile Val Ser Ala Gly Ala Gly Cys Asp Arg Asp Gly Lys
            260                 265                 270

Tyr Gly Phe Tyr Thr His Val Phe Arg Leu Lys Lys Trp Ile Gln Lys
        275                 280                 285

Val Ile Asp Gln Phe Gly Glu
    290                 295

<210> SEQ ID NO 2
<211> LENGTH: 295
<212> TYPE: PRT
<213> ORGANISM: Artificial sequence
<220> FEATURE:
<223> OTHER INFORMATION: synthetic sequence

<400> SEQUENCE: 2

Thr Phe Gly Ser Gly Glu Ala Asp Cys Gly Leu Arg Pro Leu Phe Glu
1               5                   10                  15

Lys Lys Ser Leu Glu Asp Lys Thr Glu Arg Glu Leu Leu Glu Ser Tyr
            20                  25                  30

Ile Asp Gly Arg Ile Val Glu Gly Ser Asp Ala Glu Ile Gly Met Ser
        35                  40                  45

Pro Trp Gln Val Met Leu Phe Arg Lys Ser Pro Gln Glu Leu Leu Cys
    50                  55                  60

Gly Ala Ser Leu Ile Ser Asp Arg Trp Val Leu Thr Ala Ala His Cys
65                  70                  75                  80

Leu Leu Tyr Pro Pro Trp Asp Lys Asn Phe Thr Glu Asn Asp Leu Leu
                85                  90                  95

Val Arg Ile Gly Lys His Ser Arg Thr Arg Tyr Glu Arg Asn Ile Glu
            100                 105                 110

Lys Ile Ser Met Leu Glu Lys Ile Tyr Ile His Pro Arg Tyr Asn Trp
        115                 120                 125

Arg Glu Asn Leu Asp Arg Asp Ile Ala Leu Met Lys Leu Lys Lys Pro
    130                 135                 140

```
Val Ala Phe Ser Asp Tyr Ile His Pro Val Cys Leu Pro Asp Arg Glu
145                 150                 155                 160

Thr Ala Ala Ser Leu Leu Gln Ala Gly Tyr Lys Gly Arg Val Thr Gly
            165                 170                 175

Trp Gly Asn Leu Lys Glu Thr Trp Thr Ala Asn Val Gly Lys Gly Gln
        180                 185                 190

Pro Ser Val Leu Gln Val Val Asn Leu Pro Ile Val Glu Arg Pro Val
    195                 200                 205

Cys Lys Asp Ser Thr Arg Ile Arg Ile Thr Asp Asn Met Phe Cys Ala
210                 215                 220

Gly Tyr Lys Pro Asp Glu Gly Lys Arg Gly Asp Ala Cys Glu Gly Asp
225                 230                 235                 240

Ser Gly Gly Pro Phe Val Met Lys Ser Pro Phe Asn Asn Arg Trp Tyr
            245                 250                 255

Gln Met Gly Ile Val Ser Trp Gly Glu Gly Cys Asp Arg Asp Gly Lys
        260                 265                 270

Tyr Gly Phe Tyr Thr His Val Phe Arg Leu Lys Lys Trp Ile Gln Lys
    275                 280                 285

Val Ile Asp Gln Phe Gly Glu
290                 295

<210> SEQ ID NO 3
<211> LENGTH: 622
<212> TYPE: PRT
<213> ORGANISM: Artificial sequence
<220> FEATURE:
<223> OTHER INFORMATION: synthetic sequence

<400> SEQUENCE: 3

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205
```

```
Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
                260                 265                 270

Trp Cys Tyr Val Ala Gly Lys Pro Gly Asp Phe Gly Tyr Cys Asp Leu
            275                 280                 285

Asn Tyr Cys Glu Glu Ala Val Glu Glu Glu Thr Gly Asp Gly Leu Asp
        290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
                340                 345                 350

Arg Glu Leu Leu Glu Ser Tyr Ile Asp Gly Arg Ile Val Glu Gly Ser
            355                 360                 365

Asp Ala Glu Ile Gly Met Ser Pro Trp Gln Val Met Leu Phe Arg Lys
        370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
                420                 425                 430

Arg Tyr Glu Arg Asn Ile Glu Lys Ile Ser Met Leu Glu Lys Ile Tyr
            435                 440                 445

Ile His Pro Arg Tyr Asn Trp Arg Glu Asn Leu Asp Arg Asp Ile Ala
        450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
                500                 505                 510

Ala Asn Val Gly Lys Gly Gln Pro Ser Val Leu Gln Val Val Asn Leu
            515                 520                 525

Pro Ile Val Glu Arg Pro Val Cys Lys Asp Ser Thr Arg Ile Arg Ile
        530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
                580                 585                 590

Gly Cys Asp Arg Asp Gly Lys Tyr Gly Phe Tyr Thr His Val Phe Arg
            595                 600                 605

Leu Lys Lys Trp Ile Gln Lys Val Ile Asp Gln Phe Gly Glu
        610                 615                 620
```

<210> SEQ ID NO 4
<211> LENGTH: 622
<212> TYPE: PRT
<213> ORGANISM: Artificial sequence
<220> FEATURE:
<223> OTHER INFORMATION: synthetic sequence

<400> SEQUENCE: 4

```
Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asp Gly Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365
```

```
Asp Ala Glu Ile Gly Met Ser Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Ala Gly Ala
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620

<210> SEQ ID NO 5
<211> LENGTH: 308
<212> TYPE: PRT
<213> ORGANISM: Artificial sequence
<220> FEATURE:
<223> OTHER INFORMATION: synthetic sequence

<400> SEQUENCE: 5

Thr Ala Thr Ser Glu Tyr Gln Thr Phe Phe Asp Gly Arg Thr Phe Gly
1               5                   10                  15

Ser Gly Glu Ala Asp Cys Gly Leu Arg Pro Leu Phe Glu Lys Lys Ser
            20                  25                  30

Leu Glu Asp Lys Thr Glu Arg Glu Leu Leu Glu Ser Tyr Ile Asp Gly
        35                  40                  45

Arg Ile Val Glu Gly Ser Asp Ala Glu Ile Gly Met Ser Pro Trp Gln
    50                  55                  60

Val Met Leu Phe Arg Lys Ser Pro Gln Glu Leu Leu Cys Gly Ala Ser
65                  70                  75                  80

Leu Ile Ser Asp Arg Trp Val Leu Thr Ala Ala His Cys Leu Leu Tyr
                85                  90                  95

Pro Pro Trp Asp Lys Asn Phe Thr Glu Asn Asp Leu Leu Val Arg Ile
            100                 105                 110
```

```
Gly Lys His Ser Arg Thr Arg Tyr Glu Arg Asn Ile Glu Lys Ile Ser
            115                 120                 125

Met Leu Glu Lys Ile Tyr Ile His Pro Arg Tyr Asn Trp Arg Glu Asn
130                 135                 140

Leu Asp Arg Asp Ile Ala Leu Met Lys Leu Lys Lys Pro Val Ala Phe
145                 150                 155                 160

Ser Asp Tyr Ile His Pro Val Cys Leu Pro Asp Arg Glu Thr Ala Ala
                165                 170                 175

Ser Leu Leu Gln Ala Gly Tyr Lys Gly Arg Val Thr Gly Trp Gly Asn
            180                 185                 190

Leu Lys Glu Thr Trp Thr Ala Asn Val Gly Lys Gly Gln Pro Ser Val
        195                 200                 205

Leu Gln Val Val Asn Leu Pro Ile Val Glu Arg Pro Val Cys Lys Asp
    210                 215                 220

Ser Thr Arg Ile Arg Ile Thr Asp Asn Met Phe Cys Ala Gly Tyr Lys
225                 230                 235                 240

Pro Asp Glu Gly Lys Arg Gly Asp Ala Cys Glu Gly Asp Ser Gly Gly
                245                 250                 255

Pro Phe Val Met Lys Ser Pro Phe Asn Asn Arg Trp Tyr Gln Met Gly
            260                 265                 270

Ile Val Ser Ala Gly Ala Gly Cys Asp Arg Asp Gly Lys Tyr Gly Phe
        275                 280                 285

Tyr Thr His Val Phe Arg Leu Lys Lys Trp Ile Gln Lys Val Ile Asp
    290                 295                 300

Gln Phe Gly Glu
305

<210> SEQ ID NO 6
<211> LENGTH: 622
<212> TYPE: PRT
<213> ORGANISM: Artificial sequence
<220> FEATURE:
<223> OTHER INFORMATION: synthetic sequence

<400> SEQUENCE: 6

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160
```

-continued

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asp Gly Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu

```
                      580                 585                 590
Gly Cys Asp Arg Asp Gly Lys Tyr Gly Phe Tyr Thr His Val Phe Arg
                595                 600                 605

Leu Lys Lys Trp Ile Gln Lys Val Ile Asp Gln Phe Gly Glu
            610                 615                 620

<210> SEQ ID NO 7
<211> LENGTH: 308
<212> TYPE: PRT
<213> ORGANISM: Artificial sequence
<220> FEATURE:
<223> OTHER INFORMATION: synthetic sequence

<400> SEQUENCE: 7

Thr Ala Thr Ser Glu Tyr Gln Thr Phe Phe Asp Gly Arg Thr Phe Gly
1               5                   10                  15

Ser Gly Glu Ala Asp Cys Gly Leu Arg Pro Leu Phe Glu Lys Lys Ser
            20                  25                  30

Leu Glu Asp Lys Thr Glu Arg Glu Leu Leu Ser Tyr Ile Asp Gly
        35                  40                  45

Arg Ile Val Glu Gly Ser Asp Ala Glu Ile Gly Met Ser Pro Trp Gln
    50                  55                  60

Val Met Leu Phe Arg Lys Ser Pro Gln Glu Leu Leu Cys Gly Ala Ser
65                  70                  75                  80

Leu Ile Ser Asp Arg Trp Val Leu Thr Ala Ala His Cys Leu Leu Tyr
                85                  90                  95

Pro Pro Trp Asp Lys Asn Phe Thr Glu Asn Asp Leu Leu Val Arg Ile
            100                 105                 110

Gly Lys His Ser Arg Thr Arg Tyr Glu Arg Asn Ile Glu Lys Ile Ser
        115                 120                 125

Met Leu Glu Lys Ile Tyr Ile His Pro Arg Tyr Asn Trp Arg Glu Asn
    130                 135                 140

Leu Asp Arg Asp Ile Ala Leu Met Lys Leu Lys Lys Pro Val Ala Phe
145                 150                 155                 160

Ser Asp Tyr Ile His Pro Val Cys Leu Pro Asp Arg Glu Thr Ala Ala
                165                 170                 175

Ser Leu Leu Gln Ala Gly Tyr Lys Gly Arg Val Thr Gly Trp Gly Asn
            180                 185                 190

Leu Lys Glu Thr Trp Thr Ala Asn Val Gly Lys Gly Gln Pro Ser Val
        195                 200                 205

Leu Gln Val Val Asn Leu Pro Ile Val Glu Arg Pro Val Cys Lys Asp
    210                 215                 220

Ser Thr Arg Ile Arg Ile Thr Asp Asn Met Phe Cys Ala Gly Tyr Lys
225                 230                 235                 240

Pro Asp Glu Gly Lys Arg Gly Asp Ala Cys Glu Gly Asp Ser Gly Gly
                245                 250                 255

Pro Phe Val Met Lys Ser Pro Phe Asn Asn Arg Trp Tyr Gln Met Gly
            260                 265                 270

Ile Val Ser Trp Gly Glu Gly Cys Asp Arg Asp Gly Lys Tyr Gly Phe
        275                 280                 285

Tyr Thr His Val Phe Arg Leu Lys Lys Trp Ile Gln Lys Val Ile Asp
    290                 295                 300

Gln Phe Gly Glu
305
```

```
<210> SEQ ID NO 8
<211> LENGTH: 301
<212> TYPE: PRT
<213> ORGANISM: Artificial sequence
<220> FEATURE:
<223> OTHER INFORMATION: synthetic sequence

<400> SEQUENCE: 8

Thr Ala Thr Ser Glu Tyr Gln Thr Phe Phe Asp Gly Arg Thr Phe Gly
1               5                   10                  15

Ser Gly Glu Ala Asp Cys Gly Leu Arg Pro Leu Phe Glu Lys Lys Ser
                20                  25                  30

Leu Glu Asp Lys Thr Glu Arg Glu Leu Leu Glu Ser Tyr Ile Asp Gly
            35                  40                  45

Arg Ile Val Glu Gly Ser Asp Ala Glu Ile Gly Met Ser Pro Trp Gln
        50                  55                  60

Val Met Leu Phe Arg Lys Ser Pro Gln Glu Leu Leu Cys Gly Ala Ser
65                  70                  75                  80

Leu Ile Ser Asp Arg Trp Val Leu Thr Ala Ala His Cys Leu Leu Tyr
                85                  90                  95

Pro Pro Trp Asp Lys Asn Phe Thr Glu Asn Asp Leu Leu Val Arg Ile
                100                 105                 110

Gly Lys His Ser Arg Thr Arg Tyr Glu Arg Asn Ile Glu Lys Ile Ser
            115                 120                 125

Met Leu Glu Lys Ile Tyr Ile His Pro Arg Tyr Asn Trp Arg Glu Asn
        130                 135                 140

Leu Asp Arg Asp Ile Ala Leu Met Lys Leu Lys Lys Pro Val Ala Phe
145                 150                 155                 160

Ser Asp Tyr Ile His Pro Val Cys Leu Pro Asp Arg Glu Thr Ala Ala
                165                 170                 175

Ser Leu Leu Gln Ala Gly Tyr Lys Gly Arg Val Thr Gly Trp Gly Asn
            180                 185                 190

Leu Lys Gly Lys Gly Gln Pro Ser Val Leu Gln Val Val Asn Leu Pro
        195                 200                 205

Ile Val Glu Arg Pro Val Cys Lys Asp Ser Thr Arg Ile Arg Ile Thr
    210                 215                 220

Asp Asn Met Phe Cys Ala Gly Tyr Lys Pro Asp Glu Gly Lys Arg Gly
225                 230                 235                 240

Asp Ala Cys Glu Gly Asp Ser Gly Gly Pro Phe Val Met Lys Ser Pro
                245                 250                 255

Phe Asn Asn Arg Trp Tyr Gln Met Gly Ile Val Ser Trp Gly Glu Gly
            260                 265                 270

Cys Asp Arg Asp Gly Lys Tyr Gly Phe Tyr Thr His Val Phe Arg Leu
        275                 280                 285

Lys Lys Trp Ile Gln Lys Val Ile Asp Gln Phe Gly Glu
    290                 295                 300

<210> SEQ ID NO 9
<211> LENGTH: 622
<212> TYPE: PRT
<213> ORGANISM: Artificial sequence
<220> FEATURE:
<223> OTHER INFORMATION: synthetic sequence

<400> SEQUENCE: 9

Met Ala His Val Arg Gly Leu Gln Leu Pro Gly Cys Leu Ala Leu Ala
1               5                   10                  15
```

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
            35                  40                  45

Glu Glu Val Arg Lys Gly Asn Leu Glu Arg Glu Cys Val Glu Glu Thr
50                      55                  60

Cys Ser Tyr Glu Glu Ala Phe Glu Ala Leu Glu Ser Ser Thr Ala Thr
65                      70                  75                  80

Asp Val Phe Trp Ala Lys Tyr Thr Ala Cys Glu Thr Ala Arg Thr Pro
                    85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
            115                 120                 125

Cys Gln Leu Trp Arg Ser Arg Tyr Pro His Lys Pro Glu Ile Asn Ser
            130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                    165                 170                 175

Arg Arg Gln Glu Cys Ser Ile Pro Val Cys Gly Gln Asp Gln Val Thr
                    180                 185                 190

Val Ala Met Thr Pro Arg Ser Glu Gly Ser Ser Val Asn Leu Ser Pro
            195                 200                 205

Pro Leu Glu Gln Cys Val Pro Asp Arg Gly Gln Gln Tyr Gln Gly Arg
210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                    245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
            275                 280                 285

Asn Tyr Cys Glu Glu Ala Val Glu Glu Glu Thr Gly Asp Gly Leu Asp
            290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                    325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
            355                 360                 365

Asp Ala Glu Ile Gly Met Ser Pro Trp Gln Val Met Leu Phe Arg Lys
            370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                    405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr

```
            435                 440                 445
Ile His Pro Arg Tyr Asn Trp Arg Glu Asn Leu Asp Arg Asp Ile Ala
450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
                500                 505                 510

Ala Asn Val Gly Lys Gly Gln Pro Ser Val Leu Gln Val Val Asn Leu
                515                 520                 525

Pro Ile Val Glu Arg Pro Val Cys Lys Asp Ser Thr Arg Ile Arg Ile
530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Ala Gly Ala
                580                 585                 590

Gly Cys Asp Arg Asp Gly Lys Tyr Gly Phe Tyr Thr His Val Phe Arg
                595                 600                 605

Leu Lys Lys Trp Ile Gln Lys Val Ile Asp Gln Phe Gly Glu
610                 615                 620
```

<210> SEQ ID NO 10
<211> LENGTH: 308
<212> TYPE: PRT
<213> ORGANISM: Artificial sequence
<220> FEATURE:
<223> OTHER INFORMATION: synthetic sequence

<400> SEQUENCE: 10

```
Thr Ala Thr Ser Glu Tyr Gln Thr Phe Phe Asn Pro Arg Thr Phe Gly
1               5                   10                  15

Ser Gly Glu Ala Asp Cys Gly Leu Arg Pro Leu Phe Glu Lys Lys Ser
                20                  25                  30

Leu Glu Asp Lys Thr Glu Arg Glu Leu Leu Glu Ser Tyr Ile Asp Gly
            35                  40                  45

Arg Ile Val Glu Gly Ser Asp Ala Glu Ile Gly Met Ser Pro Trp Gln
        50                  55                  60

Val Met Leu Phe Arg Lys Ser Pro Gln Glu Leu Leu Cys Gly Ala Ser
65                  70                  75                  80

Leu Ile Ser Asp Arg Trp Val Leu Thr Ala Ala His Cys Leu Leu Tyr
                85                  90                  95

Pro Pro Trp Asp Lys Asn Phe Thr Glu Asn Asp Leu Leu Val Arg Ile
                100                 105                 110

Gly Lys His Ser Arg Thr Arg Tyr Glu Arg Asn Ile Glu Lys Ile Ser
            115                 120                 125

Met Leu Glu Lys Ile Tyr Ile His Pro Arg Tyr Asn Trp Arg Glu Asn
130                 135                 140

Leu Asp Arg Asp Ile Ala Leu Met Lys Leu Lys Lys Pro Val Ala Phe
145                 150                 155                 160

Ser Asp Tyr Ile His Pro Val Cys Leu Pro Asp Arg Glu Thr Ala Ala
                165                 170                 175

Ser Leu Leu Gln Ala Gly Tyr Lys Gly Arg Val Thr Gly Trp Gly Asn
```

```
                180                 185                 190
Leu Lys Glu Thr Trp Thr Ala Asn Val Gly Lys Gly Gln Pro Ser Val
            195                 200                 205

Leu Gln Val Val Asn Leu Pro Ile Val Glu Arg Pro Val Cys Lys Asp
        210                 215                 220

Ser Thr Arg Ile Arg Ile Thr Asp Asn Met Phe Cys Ala Gly Tyr Lys
225                 230                 235                 240

Pro Asp Glu Gly Lys Arg Gly Asp Ala Cys Glu Gly Asp Ser Gly Gly
                245                 250                 255

Pro Phe Val Met Lys Ser Pro Phe Asn Asn Arg Trp Tyr Gln Met Gly
            260                 265                 270

Ile Val Ser Ala Gly Ala Gly Cys Asp Arg Asp Gly Lys Tyr Gly Phe
        275                 280                 285

Tyr Thr His Val Phe Arg Leu Lys Lys Trp Ile Gln Lys Val Ile Asp
290                 295                 300

Gln Phe Gly Glu
305

<210> SEQ ID NO 11
<211> LENGTH: 6
<212> TYPE: PRT
<213> ORGANISM: Artificial sequence
<220> FEATURE:
<223> OTHER INFORMATION: synthetic sequence

<400> SEQUENCE: 11

Phe Asn Pro Arg Thr Phe
1               5

<210> SEQ ID NO 12
<211> LENGTH: 6
<212> TYPE: PRT
<213> ORGANISM: Artificial sequence
<220> FEATURE:
<223> OTHER INFORMATION: synthetic sequence

<400> SEQUENCE: 12

Phe Asp Gly Arg Thr Phe
1               5

<210> SEQ ID NO 13
<211> LENGTH: 7
<212> TYPE: PRT
<213> ORGANISM: Artificial sequence
<220> FEATURE:
<223> OTHER INFORMATION: synthetic sequence

<400> SEQUENCE: 13

Tyr Ile Asp Gly Arg Ile Val
1               5

<210> SEQ ID NO 14
<211> LENGTH: 298
<212> TYPE: PRT
<213> ORGANISM: Artificial sequence
<220> FEATURE:
<223> OTHER INFORMATION: synthetic sequence

<400> SEQUENCE: 14

Asp Gly Arg Thr Phe Gly Ser Gly Glu Ala Asp Cys Gly Leu Arg Pro
1               5                   10                  15

Leu Phe Glu Lys Lys Ser Leu Glu Asp Lys Thr Glu Arg Glu Leu Leu
```

```
                  20                  25                  30
Glu Ser Tyr Ile Asp Gly Arg Ile Val Glu Gly Ser Asp Ala Glu Ile
            35                  40                  45
Gly Met Ser Pro Trp Gln Val Met Leu Phe Arg Lys Ser Pro Gln Glu
        50                  55                  60
Leu Leu Cys Gly Ala Ser Leu Ile Ser Asp Arg Trp Val Leu Thr Ala
65                  70                  75                  80
Ala His Cys Leu Leu Tyr Pro Pro Trp Asp Lys Asn Phe Thr Glu Asn
                85                  90                  95
Asp Leu Leu Val Arg Ile Gly Lys His Ser Arg Thr Arg Tyr Glu Arg
            100                 105                 110
Asn Ile Glu Lys Ile Ser Met Leu Glu Lys Ile Tyr Ile His Pro Arg
        115                 120                 125
Tyr Asn Trp Arg Glu Asn Leu Asp Arg Asp Ile Ala Leu Met Lys Leu
        130                 135                 140
Lys Lys Pro Val Ala Phe Ser Asp Tyr Ile His Pro Val Cys Leu Pro
145                 150                 155                 160
Asp Arg Glu Thr Ala Ala Ser Leu Leu Gln Ala Gly Tyr Lys Gly Arg
                165                 170                 175
Val Thr Gly Trp Gly Asn Leu Lys Glu Thr Trp Thr Ala Asn Val Gly
            180                 185                 190
Lys Gly Gln Pro Ser Val Leu Gln Val Val Asn Leu Pro Ile Val Glu
        195                 200                 205
Arg Pro Val Cys Lys Asp Ser Thr Arg Ile Arg Ile Thr Asp Asn Met
    210                 215                 220
Phe Cys Ala Gly Tyr Lys Pro Asp Glu Gly Lys Arg Gly Asp Ala Cys
225                 230                 235                 240
Glu Gly Asp Ser Gly Gly Pro Phe Val Met Lys Ser Pro Phe Asn Asn
                245                 250                 255
Arg Trp Tyr Gln Met Gly Ile Val Ser Ala Gly Ala Gly Cys Asp Arg
            260                 265                 270
Asp Gly Lys Tyr Gly Phe Tyr Thr His Val Phe Arg Leu Lys Lys Trp
        275                 280                 285
Ile Gln Lys Val Ile Asp Gln Phe Gly Glu
        290                 295

<210> SEQ ID NO 15
<211> LENGTH: 298
<212> TYPE: PRT
<213> ORGANISM: Artificial sequence
<220> FEATURE:
<223> OTHER INFORMATION: synthetic sequence

<400> SEQUENCE: 15

Glu Gly Arg Thr Phe Gly Ser Gly Glu Ala Asp Cys Gly Leu Arg Pro
1               5                   10                  15
Leu Phe Glu Lys Lys Ser Leu Glu Asp Lys Thr Glu Arg Glu Leu Leu
            20                  25                  30
Glu Ser Tyr Ile Asp Gly Arg Ile Val Glu Gly Ser Asp Ala Glu Ile
        35                  40                  45
Gly Met Ser Pro Trp Gln Val Met Leu Phe Arg Lys Ser Pro Gln Glu
    50                  55                  60
Leu Leu Cys Gly Ala Ser Leu Ile Ser Asp Arg Trp Val Leu Thr Ala
65                  70                  75                  80
Ala His Cys Leu Leu Tyr Pro Pro Trp Asp Lys Asn Phe Thr Glu Asn
```

```
                    85                  90                  95
Asp Leu Leu Val Arg Ile Gly Lys His Ser Arg Thr Arg Tyr Glu Arg
                100                 105                 110

Asn Ile Glu Lys Ile Ser Met Leu Glu Lys Ile Tyr Ile His Pro Arg
            115                 120                 125

Tyr Asn Trp Arg Glu Asn Leu Asp Arg Asp Ile Ala Leu Met Lys Leu
        130                 135                 140

Lys Lys Pro Val Ala Phe Ser Asp Tyr Ile His Pro Val Cys Leu Pro
145                 150                 155                 160

Asp Arg Glu Thr Ala Ala Ser Leu Leu Gln Ala Gly Tyr Lys Gly Arg
                165                 170                 175

Val Thr Gly Trp Gly Asn Leu Lys Glu Thr Trp Thr Ala Asn Val Gly
            180                 185                 190

Lys Gly Gln Pro Ser Val Leu Gln Val Val Asn Leu Pro Ile Val Glu
        195                 200                 205

Arg Pro Val Cys Lys Asp Ser Thr Arg Ile Arg Ile Thr Asp Asn Met
210                 215                 220

Phe Cys Ala Gly Tyr Lys Pro Asp Glu Gly Lys Arg Gly Asp Ala Cys
225                 230                 235                 240

Glu Gly Asp Ser Gly Gly Pro Phe Val Met Lys Ser Pro Phe Asn Asn
                245                 250                 255

Arg Trp Tyr Gln Met Gly Ile Val Ser Ala Gly Ala Gly Cys Asp Arg
            260                 265                 270

Asp Gly Lys Tyr Gly Phe Tyr Thr His Val Phe Arg Leu Lys Lys Trp
        275                 280                 285

Ile Gln Lys Val Ile Asp Gln Phe Gly Glu
290                 295

<210> SEQ ID NO 16
<211> LENGTH: 298
<212> TYPE: PRT
<213> ORGANISM: Artificial sequence
<220> FEATURE:
<223> OTHER INFORMATION: synthetic sequence

<400> SEQUENCE: 16

Asp Gly Arg Thr Phe Gly Ser Gly Glu Ala Asp Cys Gly Leu Arg Pro
1               5                   10                  15

Leu Phe Glu Lys Lys Ser Leu Glu Asp Lys Thr Glu Arg Glu Leu Leu
                20                  25                  30

Glu Ser Tyr Ile Asp Gly Arg Ile Val Glu Gly Ser Asp Ala Glu Ile
            35                  40                  45

Gly Met Ser Pro Trp Gln Val Met Leu Phe Arg Lys Ser Pro Gln Glu
        50                  55                  60

Leu Leu Cys Gly Ala Ser Leu Ile Ser Asp Arg Trp Val Leu Thr Ala
65                  70                  75                  80

Ala His Cys Leu Leu Tyr Pro Pro Trp Asp Lys Asn Phe Thr Glu Asn
                85                  90                  95

Asp Leu Leu Val Arg Ile Gly Lys His Ser Arg Thr Arg Tyr Glu Arg
                100                 105                 110

Asn Ile Glu Lys Ile Ser Met Leu Glu Lys Ile Tyr Ile His Pro Arg
            115                 120                 125

Tyr Asn Trp Arg Glu Asn Leu Asp Arg Asp Ile Ala Leu Met Lys Leu
        130                 135                 140

Lys Lys Pro Val Ala Phe Ser Asp Tyr Ile His Pro Val Cys Leu Pro
```

```
145                 150                 155                 160
Asp Arg Glu Thr Ala Ala Ser Leu Leu Gln Ala Gly Tyr Lys Gly Arg
                165                 170                 175

Val Thr Gly Trp Gly Asn Leu Lys Glu Thr Trp Thr Ala Asn Val Gly
            180                 185                 190

Lys Gly Gln Pro Ser Val Leu Gln Val Val Asn Leu Pro Ile Val Glu
        195                 200                 205

Arg Pro Val Cys Lys Asp Ser Thr Arg Ile Arg Ile Thr Asp Asn Met
    210                 215                 220

Phe Cys Ala Gly Tyr Lys Pro Asp Glu Gly Lys Arg Gly Asp Ala Cys
225                 230                 235                 240

Glu Gly Asp Ser Gly Gly Pro Phe Val Met Lys Ser Pro Phe Asn Asn
                245                 250                 255

Arg Trp Tyr Gln Met Gly Ile Val Ser Trp Gly Glu Gly Cys Asp Arg
            260                 265                 270

Asp Gly Lys Tyr Gly Phe Tyr Thr His Val Phe Arg Leu Lys Lys Trp
        275                 280                 285

Ile Gln Lys Val Ile Asp Gln Phe Gly Glu
    290                 295

<210> SEQ ID NO 17
<211> LENGTH: 298
<212> TYPE: PRT
<213> ORGANISM: Artificial sequence
<220> FEATURE:
<223> OTHER INFORMATION: synthetic sequence

<400> SEQUENCE: 17

Glu Gly Arg Thr Phe Gly Ser Gly Glu Ala Asp Cys Gly Leu Arg Pro
1               5                   10                  15

Leu Phe Glu Lys Lys Ser Leu Glu Asp Lys Thr Glu Arg Glu Leu Leu
            20                  25                  30

Glu Ser Tyr Ile Asp Gly Arg Ile Val Glu Gly Ser Asp Ala Glu Ile
        35                  40                  45

Gly Met Ser Pro Trp Gln Val Met Leu Phe Arg Lys Ser Pro Gln Glu
    50                  55                  60

Leu Leu Cys Gly Ala Ser Leu Ile Ser Asp Arg Trp Val Leu Thr Ala
65              70                  75                  80

Ala His Cys Leu Leu Tyr Pro Pro Trp Asp Lys Asn Phe Thr Glu Asn
                85                  90                  95

Asp Leu Leu Val Arg Ile Gly Lys His Ser Arg Thr Arg Tyr Glu Arg
            100                 105                 110

Asn Ile Glu Lys Ile Ser Met Leu Glu Lys Ile Tyr Ile His Pro Arg
        115                 120                 125

Tyr Asn Trp Arg Glu Asn Leu Asp Arg Asp Ile Ala Leu Met Lys Leu
    130                 135                 140

Lys Lys Pro Val Ala Phe Ser Asp Tyr Ile His Pro Val Cys Leu Pro
145                 150                 155                 160

Asp Arg Glu Thr Ala Ala Ser Leu Leu Gln Ala Gly Tyr Lys Gly Arg
                165                 170                 175

Val Thr Gly Trp Gly Asn Leu Lys Glu Thr Trp Thr Ala Asn Val Gly
            180                 185                 190

Lys Gly Gln Pro Ser Val Leu Gln Val Val Asn Leu Pro Ile Val Glu
        195                 200                 205

Arg Pro Val Cys Lys Asp Ser Thr Arg Ile Arg Ile Thr Asp Asn Met
```

```
                    210                 215                 220

Phe Cys Ala Gly Tyr Lys Pro Asp Glu Gly Lys Arg Gly Asp Ala Cys
225                 230                 235                 240

Glu Gly Asp Ser Gly Gly Pro Phe Val Met Lys Ser Pro Phe Asn Asn
                245                 250                 255

Arg Trp Tyr Gln Met Gly Ile Val Ser Trp Gly Glu Gly Cys Asp Arg
                260                 265                 270

Asp Gly Lys Tyr Gly Phe Tyr Thr His Val Phe Arg Leu Lys Lys Trp
            275                 280                 285

Ile Gln Lys Val Ile Asp Gln Phe Gly Glu
            290                 295

<210> SEQ ID NO 18
<211> LENGTH: 579
<212> TYPE: PRT
<213> ORGANISM: Artificial sequence
<220> FEATURE:
<223> OTHER INFORMATION: synthetic sequence

<400> SEQUENCE: 18

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
                20                  25                  30

Ser Ser Thr Ala Thr Asp Val Phe Trp Ala Lys Tyr Thr Ala Cys Glu
            35                  40                  45

Thr Ala Arg Thr Pro Arg Asp Lys Leu Ala Ala Cys Leu Glu Gly Asn
        50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
                100                 105                 110

Phe Cys Arg Asn Pro Asp Ser Ser Thr Thr Gly Pro Trp Cys Tyr Thr
            115                 120                 125

Thr Asp Pro Thr Val Arg Arg Gln Glu Cys Ser Ile Pro Val Cys Gly
        130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
```

```
                275                 280                 285
Gly Glu Ala Asp Cys Gly Leu Arg Pro Leu Phe Glu Lys Lys Ser Leu
290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 19
<211> LENGTH: 579
<212> TYPE: PRT
<213> ORGANISM: Artificial sequence
<220> FEATURE:
<223> OTHER INFORMATION: synthetic sequence

<400> SEQUENCE: 19

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60
```

```
Cys Ala Glu Gly Leu Gly Thr Asn Tyr Arg Gly His Val Asn Ile Thr
 65                  70                  75                  80

Arg Ser Gly Ile Glu Cys Gln Leu Trp Arg Ser Arg Tyr Pro His Lys
                 85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
        370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
450                 455                 460

Lys Glu Thr Trp Thr Ala Asn Val Gly Lys Gly Gln Pro Ser Val Leu
465                 470                 475                 480
```

-continued

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Ala Gly Ala Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 20
<211> LENGTH: 579
<212> TYPE: PRT
<213> ORGANISM: Artificial sequence
<220> FEATURE:
<223> OTHER INFORMATION: synthetic sequence

<400> SEQUENCE: 20

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr

```
                    260                 265                 270
Ala Thr Ser Glu Tyr Gln Thr Phe Phe Asp Gly Arg Thr Phe Gly Ser
                275                 280                 285

Gly Glu Ala Asp Cys Gly Leu Arg Pro Leu Phe Glu Lys Lys Ser Leu
            290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Ala Gly Ala Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 21
<211> LENGTH: 579
<212> TYPE: PRT
<213> ORGANISM: Artificial sequence
<220> FEATURE:
<223> OTHER INFORMATION: synthetic sequence

<400> SEQUENCE: 21

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
                20                  25                  30

Ser Ser Thr Ala Thr Asp Val Phe Trp Ala Lys Tyr Thr Ala Cys Glu
            35                  40                  45
```

```
Thr Ala Arg Thr Pro Arg Asp Lys Leu Ala Ala Cys Leu Glu Gly Asn
     50                  55                  60

Cys Ala Glu Gly Leu Gly Thr Asn Tyr Arg Gly His Val Asn Ile Thr
 65                  70                  75                  80

Arg Ser Gly Ile Glu Cys Gln Leu Trp Arg Ser Arg Tyr Pro His Lys
                 85                  90                  95

Pro Glu Ile Asn Ser Thr Thr His Pro Gly Ala Asp Leu Gln Glu Asn
             100                 105                 110

Phe Cys Arg Asn Pro Asp Ser Ser Thr Thr Gly Pro Trp Cys Tyr Thr
         115                 120                 125

Thr Asp Pro Thr Val Arg Arg Gln Glu Cys Ser Ile Pro Val Cys Gly
     130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                 165                 170                 175

Gln Tyr Gln Gly Arg Leu Ala Val Thr Thr His Gly Leu Pro Cys Leu
             180                 185                 190

Ala Trp Ala Ser Ala Gln Ala Lys Ala Leu Ser Lys His Gln Asp Phe
     195                 200                 205

Asn Ser Ala Val Gln Leu Val Glu Asn Phe Cys Arg Asn Pro Asp Gly
210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                 245                 250                 255

Gly Asp Gly Leu Asp Glu Asp Ser Asp Arg Ala Ile Glu Gly Arg Thr
             260                 265                 270

Ala Thr Ser Glu Tyr Gln Thr Phe Phe Glu Gly Arg Thr Phe Gly Ser
     275                 280                 285

Gly Glu Ala Asp Cys Gly Leu Arg Pro Leu Phe Glu Lys Lys Ser Leu
290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                 325                 330                 335

Met Leu Phe Arg Lys Ser Pro Gln Glu Leu Leu Cys Gly Ala Ser Leu
             340                 345                 350

Ile Ser Asp Arg Trp Val Leu Thr Ala Ala His Cys Leu Leu Tyr Pro
     355                 360                 365

Pro Trp Asp Lys Asn Phe Thr Glu Asn Asp Leu Leu Val Arg Ile Gly
     370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                 405                 410                 415

Asp Arg Asp Ile Ala Leu Met Lys Leu Lys Lys Pro Val Ala Phe Ser
             420                 425                 430

Asp Tyr Ile His Pro Val Cys Leu Pro Asp Arg Glu Thr Ala Ala Ser
     435                 440                 445

Leu Leu Gln Ala Gly Tyr Lys Gly Arg Val Thr Gly Trp Gly Asn Leu
     450                 455                 460
```

```
Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
            485                 490                 495

Thr Arg Ile Arg Ile Thr Asp Asn Met Phe Cys Ala Gly Tyr Lys Pro
        500                 505                 510

Asp Glu Gly Lys Arg Gly Asp Ala Cys Glu Gly Asp Ser Gly Gly Pro
    515                 520                 525

Phe Val Met Lys Ser Pro Phe Asn Asn Arg Trp Tyr Gln Met Gly Ile
530                 535                 540

Val Ser Ala Gly Ala Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 22
<211> LENGTH: 298
<212> TYPE: PRT
<213> ORGANISM: Artificial sequence
<220> FEATURE:
<223> OTHER INFORMATION: synthetic sequence

<400> SEQUENCE: 22

Asp Gly Arg Thr Phe Gly Ser Gly Glu Ala Asp Cys Gly Leu Arg Pro
1               5                   10                  15

Leu Phe Glu Lys Lys Ser Leu Glu Asp Lys Thr Glu Arg Glu Leu Leu
            20                  25                  30

Glu Ser Tyr Ile Asp Gly Arg Ile Val Glu Gly Ser Asp Ala Glu Ile
        35                  40                  45

Gly Met Ser Pro Trp Gln Val Met Leu Phe Arg Lys Ser Pro Gln Glu
50                  55                  60

Leu Leu Cys Gly Ala Ser Leu Ile Ser Asp Arg Trp Val Leu Thr Ala
65                  70                  75                  80

Ala His Cys Leu Leu Tyr Pro Pro Trp Asp Lys Asn Phe Thr Glu Asn
                85                  90                  95

Asp Leu Leu Val Arg Ile Gly Lys His Ser Arg Thr Arg Tyr Glu Arg
            100                 105                 110

Asn Ile Glu Lys Ile Ser Met Leu Glu Lys Ile Tyr Ile His Pro Arg
        115                 120                 125

Tyr Asn Trp Arg Glu Asn Leu Asp Arg Asp Ile Ala Leu Met Lys Leu
130                 135                 140

Lys Lys Pro Val Ala Phe Ser Asp Tyr Ile His Pro Val Cys Leu Pro
145                 150                 155                 160

Asp Arg Glu Thr Ala Ala Ser Leu Leu Gln Ala Gly Tyr Lys Gly Arg
                165                 170                 175

Val Thr Gly Trp Gly Asn Leu Lys Glu Thr Trp Thr Ala Asn Val Gly
            180                 185                 190

Lys Gly Gln Pro Ser Val Leu Gln Val Val Asn Leu Pro Ile Val Glu
        195                 200                 205

Arg Pro Val Cys Lys Asp Ser Thr Arg Ile Arg Ile Thr Asp Asn Met
    210                 215                 220

Phe Cys Ala Gly Tyr Lys Pro Asp Glu Gly Lys Arg Gly Asp Ala Cys
225                 230                 235                 240

Glu Gly Asp Ser Gly Gly Pro Phe Val Met Lys Ser Pro Phe Asn Asn
```

```
            245                 250                 255
Arg Trp Tyr Gln Met Gly Ile Val Ser Ala Gly Ala Gly Cys Asp Arg
            260                 265                 270

Asp Gly Lys Tyr Gly Phe Tyr Thr His Val Phe Arg Leu Lys Lys Trp
        275                 280                 285

Ile Gln Lys Val Ile Asp Gln Phe Gly Glu
        290                 295

<210> SEQ ID NO 23
<211> LENGTH: 298
<212> TYPE: PRT
<213> ORGANISM: Artificial sequence
<220> FEATURE:
<223> OTHER INFORMATION: synthetic sequence

<400> SEQUENCE: 23

Glu Gly Arg Thr Phe Gly Ser Gly Glu Ala Asp Cys Gly Leu Arg Pro
1               5                   10                  15

Leu Phe Glu Lys Lys Ser Leu Glu Asp Lys Thr Glu Arg Glu Leu Leu
            20                  25                  30

Glu Ser Tyr Ile Asp Gly Arg Ile Val Glu Gly Ser Asp Ala Glu Ile
        35                  40                  45

Gly Met Ser Pro Trp Gln Val Met Leu Phe Arg Lys Ser Pro Gln Glu
    50                  55                  60

Leu Leu Cys Gly Ala Ser Leu Ile Ser Asp Arg Trp Val Leu Thr Ala
65                  70                  75                  80

Ala His Cys Leu Leu Tyr Pro Pro Trp Asp Lys Asn Phe Thr Glu Asn
                85                  90                  95

Asp Leu Leu Val Arg Ile Gly Lys His Ser Arg Thr Arg Tyr Glu Arg
            100                 105                 110

Asn Ile Glu Lys Ile Ser Met Leu Glu Lys Ile Tyr Ile His Pro Arg
        115                 120                 125

Tyr Asn Trp Arg Glu Asn Leu Asp Arg Asp Ile Ala Leu Met Lys Leu
    130                 135                 140

Lys Lys Pro Val Ala Phe Ser Asp Tyr Ile His Pro Val Cys Leu Pro
145                 150                 155                 160

Asp Arg Glu Thr Ala Ala Ser Leu Leu Gln Ala Gly Tyr Lys Gly Arg
                165                 170                 175

Val Thr Gly Trp Gly Asn Leu Lys Glu Thr Trp Thr Ala Asn Val Gly
            180                 185                 190

Lys Gly Gln Pro Ser Val Leu Gln Val Val Asn Leu Pro Ile Val Glu
        195                 200                 205

Arg Pro Val Cys Lys Asp Ser Thr Arg Ile Arg Ile Thr Asp Asn Met
    210                 215                 220

Phe Cys Ala Gly Tyr Lys Pro Asp Glu Gly Lys Arg Gly Asp Ala Cys
225                 230                 235                 240

Glu Gly Asp Ser Gly Gly Pro Phe Val Met Lys Ser Pro Phe Asn Asn
                245                 250                 255

Arg Trp Tyr Gln Met Gly Ile Val Ser Ala Gly Ala Gly Cys Asp Arg
            260                 265                 270

Asp Gly Lys Tyr Gly Phe Tyr Thr His Val Phe Arg Leu Lys Lys Trp
        275                 280                 285

Ile Gln Lys Val Ile Asp Gln Phe Gly Glu
        290                 295
```

```
<210> SEQ ID NO 24
<211> LENGTH: 298
<212> TYPE: PRT
<213> ORGANISM: Artificial sequence
<220> FEATURE:
<223> OTHER INFORMATION: synthetic sequence

<400> SEQUENCE: 24

Asp Gly Arg Thr Phe Gly Ser Gly Glu Ala Asp Cys Gly Leu Arg Pro
1               5                   10                  15

Leu Phe Glu Lys Lys Ser Leu Glu Asp Lys Thr Glu Arg Glu Leu Leu
            20                  25                  30

Glu Ser Tyr Ile Asp Gly Arg Ile Val Glu Gly Ser Asp Ala Glu Ile
        35                  40                  45

Gly Met Ser Pro Trp Gln Val Met Leu Phe Arg Lys Ser Pro Gln Glu
    50                  55                  60

Leu Leu Cys Gly Ala Ser Leu Ile Ser Asp Arg Trp Val Leu Thr Ala
65                  70                  75                  80

Ala His Cys Leu Leu Tyr Pro Pro Trp Asp Lys Asn Phe Thr Glu Asn
                85                  90                  95

Asp Leu Leu Val Arg Ile Gly Lys His Ser Arg Thr Arg Tyr Glu Arg
            100                 105                 110

Asn Ile Glu Lys Ile Ser Met Leu Glu Lys Ile Tyr Ile His Pro Arg
        115                 120                 125

Tyr Asn Trp Arg Glu Asn Leu Asp Arg Asp Ile Ala Leu Met Lys Leu
    130                 135                 140

Lys Lys Pro Val Ala Phe Ser Asp Tyr Ile His Pro Val Cys Leu Pro
145                 150                 155                 160

Asp Arg Glu Thr Ala Ala Ser Leu Leu Gln Ala Gly Tyr Lys Gly Arg
                165                 170                 175

Val Thr Gly Trp Gly Asn Leu Lys Glu Thr Trp Thr Ala Asn Val Gly
            180                 185                 190

Lys Gly Gln Pro Ser Val Leu Gln Val Val Asn Leu Pro Ile Val Glu
        195                 200                 205

Arg Pro Val Cys Lys Asp Ser Thr Arg Ile Arg Ile Thr Asp Asn Met
    210                 215                 220

Phe Cys Ala Gly Tyr Lys Pro Asp Glu Gly Lys Arg Gly Asp Ala Cys
225                 230                 235                 240

Glu Gly Asp Ser Gly Gly Pro Phe Val Met Lys Ser Pro Phe Asn Asn
                245                 250                 255

Arg Trp Tyr Gln Met Gly Ile Val Ser Trp Gly Glu Gly Cys Asp Arg
            260                 265                 270

Asp Gly Lys Tyr Gly Phe Tyr Thr His Val Phe Arg Leu Lys Lys Trp
        275                 280                 285

Ile Gln Lys Val Ile Asp Gln Phe Gly Glu
    290                 295

<210> SEQ ID NO 25
<211> LENGTH: 298
<212> TYPE: PRT
<213> ORGANISM: Artificial sequence
<220> FEATURE:
<223> OTHER INFORMATION: synthetic sequence

<400> SEQUENCE: 25

Glu Gly Arg Thr Phe Gly Ser Gly Glu Ala Asp Cys Gly Leu Arg Pro
1               5                   10                  15
```

-continued

```
Leu Phe Glu Lys Lys Ser Leu Glu Asp Lys Thr Glu Arg Glu Leu Leu
            20                  25                  30

Glu Ser Tyr Ile Asp Gly Arg Ile Val Glu Gly Ser Asp Ala Glu Ile
        35                  40                  45

Gly Met Ser Pro Trp Gln Val Met Leu Phe Arg Lys Ser Pro Gln Glu
    50                  55                  60

Leu Leu Cys Gly Ala Ser Leu Ile Ser Asp Arg Trp Val Leu Thr Ala
65                  70                  75                  80

Ala His Cys Leu Leu Tyr Pro Pro Trp Asp Lys Asn Phe Thr Glu Asn
                85                  90                  95

Asp Leu Leu Val Arg Ile Gly Lys His Ser Arg Thr Arg Tyr Glu Arg
            100                 105                 110

Asn Ile Glu Lys Ile Ser Met Leu Glu Lys Ile Tyr Ile His Pro Arg
        115                 120                 125

Tyr Asn Trp Arg Glu Asn Leu Asp Arg Asp Ile Ala Leu Met Lys Leu
    130                 135                 140

Lys Lys Pro Val Ala Phe Ser Asp Tyr Ile His Pro Val Cys Leu Pro
145                 150                 155                 160

Asp Arg Glu Thr Ala Ala Ser Leu Leu Gln Ala Gly Tyr Lys Gly Arg
                165                 170                 175

Val Thr Gly Trp Gly Asn Leu Lys Glu Thr Trp Thr Ala Asn Val Gly
            180                 185                 190

Lys Gly Gln Pro Ser Val Leu Gln Val Val Asn Leu Pro Ile Val Glu
        195                 200                 205

Arg Pro Val Cys Lys Asp Ser Thr Arg Ile Arg Ile Thr Asp Asn Met
    210                 215                 220

Phe Cys Ala Gly Tyr Lys Pro Asp Glu Gly Lys Arg Gly Asp Ala Cys
225                 230                 235                 240

Glu Gly Asp Ser Gly Gly Pro Phe Val Met Lys Ser Pro Phe Asn Asn
                245                 250                 255

Arg Trp Tyr Gln Met Gly Ile Val Ser Trp Gly Glu Gly Cys Asp Arg
            260                 265                 270

Asp Gly Lys Tyr Gly Phe Tyr Thr His Val Phe Arg Leu Lys Lys Trp
        275                 280                 285

Ile Gln Lys Val Ile Asp Gln Phe Gly Glu
    290                 295
```

The invention claimed is:

1. A bacteria-expressed E-WE thrombin precursor comprising an amino acid residue sequence of up to 622 residues that includes the amino acid residue sequence of SEQ ID NO:1 and an added ecarin cleavage site, Asp-Gly-Arg or Glu-Gly-Arg, peptide-bonded to residue Thr 285 as numbered in SEQ ID NO:20, wherein a recombinant E-WE thrombin having anticoagulant property can be prepared from ecarin-mediated cleavage of the E-WE thrombin precursor.

2. The bacteria-expressed E-WE thrombin precursor according to claim 1 that is E-WE preprothrombin of SEQ ID NO:4.

3. The bacteria-expressed E-WE thrombin precursor according to claim 1 that is E-WE prethrombin-2 of SEQ ID NO: 5.

4. The bacteria-expressed E-WE thrombin precursor according to claim 1, wherein the bacteria is *E. coli.*

5. A kit for the preparation of thrombin, said kit comprising a package containing a recombinant thrombin precursor of claim 1 in an amount sufficient for at least one use and instructions for thrombin preparation using said thrombin precursor.

6. The kit according to claim 5, further including a second package containing an effective amount of ecarin.

7. The kit according to claim 5, wherein said thrombin precursor is that of sequence of SEQ ID NOs:6 or 7.

8. The kit according to claim 5, wherein said thrombin precursor contains an amino acid residue sequence that is at least 95 percent identical to the amino acid residue sequence of wild type human thrombin of SEQ ID NO:2.

9. The kit according to claim 8, wherein said thrombin precursor is that of sequence of SEQ ID NOs:4, 5, or 8.

* * * * *